(12) United States Patent (10) Patent No.: US 8,871,899 B2
Wang et al. (45) Date of Patent: Oct. 28, 2014

(54) CONTROL OF VIRAL-HOST MEMBRANE FUSION WITH HYDROGEN BOND SURROGATE-BASED ARTIFICIAL HELICES

(75) Inventors: Deyun Wang, Elmhurst, NY (US); Paramjit Arora, White Plains, NY (US)

(73) Assignee: New York University, New York, NY (US)

( * ) Notice: Subject to any disclaimer, the term of this patent is extended or adjusted under 35 U.S.C. 154(b) by 1015 days.

(21) Appl. No.: 12/811,088

(22) PCT Filed: Dec. 31, 2008

(86) PCT No.: PCT/US2008/088667

§ 371 (c)(1),
(2), (4) Date: Nov. 5, 2010

(87) PCT Pub. No.: WO2009/110952

PCT Pub. Date: Sep. 11, 2009

(65) Prior Publication Data

US 2011/0046043 A1 Feb. 24, 2011

Related U.S. Application Data

(60) Provisional application No. 61/018,118, filed on Dec. 31, 2007.

(51) Int. Cl.
*C07K 7/08* (2006.01)
*A61K 38/00* (2006.01)
*C07K 14/005* (2006.01)

(52) U.S. Cl.
CPC ..... *C07K 14/005* (2013.01); *C12N 2740/16122* (2013.01); *A61K 38/00* (2013.01)
USPC ...................... 530/326; 530/388.35; 514/21.4

(58) Field of Classification Search
CPC ......... C07K 14/005; C07K 4/00; A61K 39/12
See application file for complete search history.

(56) References Cited

U.S. PATENT DOCUMENTS

| | | | |
|---|---|---|---|
| 5,446,128 A | 8/1995 | Kahn | |
| 5,710,245 A | 1/1998 | Kahn | |
| 5,859,184 A | 1/1999 | Kahn et al. | |
| 6,150,088 A | 11/2000 | Chan et al. | |
| 6,506,554 B1 | 1/2003 | Chan et al. | |
| 6,596,497 B1 | 7/2003 | Jiang et al. | |
| 6,818,740 B1 | 11/2004 | Eckert et al. | |
| 6,841,657 B2 | 1/2005 | Eckert et al. | |
| 7,045,552 B2 | 5/2006 | Heilman et al. | |
| 7,192,713 B1 | 3/2007 | Verdine et al. | |
| 7,202,332 B2 * | 4/2007 | Arora et al. | 530/333 |
| 7,705,118 B2 | 4/2010 | Arora et al. | |
| 7,723,469 B2 | 5/2010 | Walensky et al. | |
| 7,786,072 B2 | 8/2010 | Verdine et al. | |
| 7,811,577 B2 | 10/2010 | Bianchi et al. | |
| 8,071,541 B2 | 12/2011 | Arora et al. | |
| 2003/0082525 A1 | 5/2003 | Root et al. | |
| 2005/0267293 A1 * | 12/2005 | Bousquet-Gagnon et al. | 530/363 |
| 2006/0014675 A1 * | 1/2006 | Arora et al. | 514/9 |
| 2007/0197772 A1 | 8/2007 | Arora et al. | |
| 2008/0262200 A1 | 10/2008 | Nash | |
| 2009/0047711 A1 | 2/2009 | Nash | |
| 2009/0088553 A1 | 4/2009 | Nash | |
| 2009/0149630 A1 | 6/2009 | Walensky et al. | |
| 2009/0176964 A1 | 7/2009 | Walensky et al. | |
| 2010/0184628 A1 | 7/2010 | Nash | |
| 2010/0184645 A1 | 7/2010 | Verdine et al. | |
| 2010/0216688 A1 | 8/2010 | Nash et al. | |
| 2010/0234563 A1 | 9/2010 | Arora et al. | |
| 2010/0298201 A1 | 11/2010 | Nash et al. | |
| 2011/0028753 A1 | 2/2011 | Verdine et al. | |
| 2011/0223149 A1 | 9/2011 | Nash et al. | |

FOREIGN PATENT DOCUMENTS

| | | |
|---|---|---|
| WO | 2005/118620 A2 | 12/2005 |
| WO | WO 2009/108261 A2 | 9/2009 |
| WO | WO 2009/108261 A3 | 1/2010 |

OTHER PUBLICATIONS

Stephens et. al. Inhibiting HIV fusion with a Beta-peptide foldamer, J Chem. Soc.; 127 (38): 13126-7 (Sep. 28, 2005).*
U.S. Appl. No. 13/119,108, filed Jun. 20, 2011, Arora et al.
U.S. Appl. No. 13/097,930, filed Apr. 29, 2011, Nash.
Andrews, et al. Forming Stable Helical Peptides Using Natural and Artificial Amino Acids. Tetrahedron. 1999; 55:11711-11743.
Angel, et al. The Role of Jun, Fos and the AP-1 Complex in Cell-proliferation and Transformation. Biochim Biophys. Acta. 1991; 1072:129-157.
Arora, "Hydrogen Bond Surrogate Approach for the Synthesis of Short α-Helical Peptides," American Chemical Society Meeting, Philadelphia (Aug. 2004) (abstract of oral presentation).
Austin, et al. A Template for Stabilization of a Peptide α-Helix: Synthesis and Evaluation of Conformational Effects by Circular Dichroism and NMR. J. Am. Chem. Soc. 1997; 119:6461-6472.
Banerji et al. Synthesis of Cyclic β-Turn Mimics from L-Pro-Phe/Phe-L-Pro Derived Di- and Tripeptides via Ring Closing Metathesis: The Role of Chirality of the Phe Residue During Cyclization. Tetrahedron Lett. 2002; 43:6473-6477.
Bianchi, et al. Covalent stabilization of coiled coils of the HIV gp41 N region yields extremely potent and broad inhibitors of viral infection. Proc Natl Acad Sci U S A. Sep. 6, 2005;102(36):12903-8. Epub Aug. 29, 2005.
Bierzynski, et al. A Salt Bridge Stabilizes the Helix Formed by Isolated C-Peptide of RNase A. Proc. Nat'l Acad. Sci. USA. 1982; 79:2470-2474.
Bird, et al. Hydrocarbon double-stapling remedies the proteolytic instability of a lengthy peptide therapeutic. Proc Natl Acad Sci U S A. Aug. 10, 2010;107(32):14093-8. Epub Jul. 21, 2010.

(Continued)

*Primary Examiner* — James H Alstrum Acevedo
*Assistant Examiner* — Jeanette Lieb
(74) *Attorney, Agent, or Firm* — LeClairRyan, a Professional Corporation

(57) ABSTRACT

The present invention relates to a peptide having one or more stable, internally-constrained HBS α-helices, where the peptide mimics at least a portion of a class I C-peptide helix or at least a portion of a class I N-peptide helix of a viral (e.g., HIV-I) coiled-coil assembly. Methods of inhibiting viral infectivity of a subject by administering these peptides are also disclosed.

5 Claims, 12 Drawing Sheets

(56) References Cited

OTHER PUBLICATIONS

Blackwell, et al. Highly Efficient Synthesis of Covalently Cross-linked Peptide Helices by Ring-closing Metathesis. Angew. Chem. Int. Ed. 1998; 37(23):3281-3284.

Bracken et al. Synthesis and Nuclear Magnetic Resonance Structure Determination of an α-Helical, Bicyclic, Lactam-bridged Hexapeptide. J. Am. Chem. Soc. 1994; 116:6431-6432.

Brunel, et al. Synthesis of constrained helical peptides by thioether ligation: application to analogs of gp41. Chem Commun (Camb). May 28, 2005;(20):2552-4. Epub Mar. 11, 2005.

Burfield, et al. Desiccant Efficiency in Solvent Drying. 3. Dipolar Aprotic Solvents. J. Org. Chem. 1978; 43(20):3966-3968.

Cabezas, et al. The Hydrogen Bond Mimic Approach: Solid-phase Synthesis of a Peptide Stabilized as an α-Helix with a Hydrazone Link. J. Am. Chem. Soc. 1999; 121:3862-3875.

Cardoso, et al. Structural basis of enhanced binding of extended and helically constrained peptide epitopes of the broadly neutralizing HIV-1 antibody 4E10. J Mol Biol. Feb. 2, 2007;365(5):1533-44. Epub Nov. 10, 2006.

Chakrabartty, et al. Helix Capping Propensities in Peptides Parallel Those in Proteins. Proc. Nat'l Acad. Sci. USA. 1993; 90:11332-11336.

Chakrabartty, et al. Helix Propensities of the Amino Acids Measured in Alanine-based Peptides without Helix-stabilizing Side-chain Interactions. Protein Sci. 1994; 3:843-852.

Chan, et al. Core structure of gp41 from the HIV envelope glycoprotein. Cell. Apr. 18, 1997;89(2):263-73.

Chapman, et al. A highly stable short alpha-helix constrained by a main-chain hydrogen-bond surrogate. J Am Chem Soc. Oct. 6, 2004;126(39):12252-3.

Chapman, et al. Optimized synthesis of hydrogen-bond surrogate helices: surprising effects of microwave heating on the activity of Grubbs catalysts. Org Lett. Dec. 7, 2006;8(25):5825-8.

Chen, et al. Determination of the Secondary Structures of Proteins by Circular Dichroism and Optical Rotatory Dispersion. Biochemistry. 1972; 11(22):4120-4131.

Chen, et al. Structure of the DNA-binding Domains from NFAT, Fos and Jun Bound Specifically to DNA, Nature. 1998; 392:42-48.

Chène, et al. Study of the Cytotoxic Effect of a Peptidic Inhibitor of the p53-hdm2 Interaction in Tumor Cells. FEBS Lett. 2002; 529:293-297.

Chène. Inhibiting the p53-MDM2 Interaction: an Important Target for Cancer Therapy. Nat Rev. Cancer. 2003; 3:102-109.

Chin, et al. Circular Dichroism Spectra of Short, Fixed-nucleus Alanine Helices. Proc. Nat'l Acad. Sci. USA. 2002; 99(24):15416-15421.

Chin, et al. Design and Evolution of a Miniature Bcl-2 Binding Protein. Angew. Chem. Int. Ed. 2001; 40(20):3806-3809.

Cory, et al. The Bcl-2 Family: Roles in Cell Survival and Oncogenesis. Oncogene. 2003; 22:8590-8607.

Daugherty, et al. A Fluorescence Assay for Leucine Zipper Dimerization: Avoiding Unintended Consequences of Fluorophore Attachment. J. Am. Chem. Soc. 1999; 121:4325-4333.

Degterev, et al. Identification of Small-molecule Inhibitors of Interaction between the BH3 Domain and Bcl-xL. Nature Cell Biol. 2001; 3:173-182.

Deng, et al. Protein design of a bacterially expressed HIV-1 gp41 fusion inhibitor. Biochemistry. Apr. 10, 2007;46(14):4360-9. Epub Mar. 20, 2007.

Dimartino, et al. Solid-phase synthesis of hydrogen-bond surrogate-derived alpha-helices. Org Lett. Jun. 9, 2005;7(12):2389-92.

Dutch, et al. Virus membrane fusion proteins: biological machines that undergo a metamorphosis. Biosci Rep. Dec. 2000;20(6):597-612.

Eckert, et al. Mechanisms of Viral Membrane Fusion and Its Inhibition. Annu. Rev. Biochem. 2001; 70:777-810.

English, et al. Rational development of beta-peptide inhibitors of human cytomegalovirus entry. J Biol Chem. Feb. 3, 2006;281(5):2661-7. Epub Nov. 7, 2005.

Ernst, et al. Design of a protein surface antagonist based on alpha-helix mimicry: inhibition of gp41 assembly and viral fusion. Angew Chem Int Ed Engl. Jan. 18, 2002;41(2):278-81.

Felix, et al. Synthesis, Biological Activity and Conformational Analysis of Cyclic GRF Analogs. Int. J. Pep. Protein Res. 1988; 32:441-454.

Ferrer, et al. Selection of gp41-mediated HIV-1 cell entry inhibitors from biased combinatorial libraries of non-natural binding elements. Nat Struct Biol. Oct. 1999;6(10):953-60.

Frey, et al. Small molecules that bind the inner core of gp41 and inhibit HIV envelope-mediated fusion. Proc Natl Acad Sci U S A. Sep. 19, 2006;103(38):13938-43. Epub Sep. 8, 2006.

García-Echeverría, et al. Discovery of Potent Antagonists of the Interaction between Human Double Minute 2 and Tumor Suppressor p53. J. Med. Chem. 2000; 43:3205-3208.

Geistlinger, et al. An Inhibitor of the Interaction of Thyroid Hormone Receptor β and Glucocorticoid Interacting Protein 1. J. Am. Chem. Soc. 2001; 123:1525-1526.

Gemperli, et al. Paralog-selective Ligands for Bcl-2 Proteins. J. Am. Chem. Soc. 2005; 127:1596-1597.

Ghadiri, et al. Secondary Structure Nucleation in Peptides. Transition Metal Ion Stabilized α-Helices. J. Am. Chem. Soc. 1990; 112:1630-1632.

Glover, et al. Crystal Structure of the Heterodimeric bZIP Transcription Factor c-Fos-c-Jun Bound to DNA. Nature. 1995; 373:257-261.

Hoveyda, et al. Ru Complexes Bearing Bidentate Carbenes: From Innocent Curiosity to Uniquely Effective Catalysts for Olefin Metathesis. Org. Biomolec. Chem. 2004; 2:8-23.

International search report dated May 11, 2006 for PCT Application No. US2005/016894.

Jackson et al., "General Approach to the Synthesis of Short α-Helical Peptides," J. Am. Chem. Soc. 113:9391-9392 (1991).

Judice, et al. Inhibition of HIV type 1 infectivity by constrained α-helical peptides: Implications for the viral fusion mechanism. Proc Natl Acad Sci U S A. Dec. 9, 1997;94(25):13426-30.

Kaul, et al. Stereochemical Control of Peptide Folding. Bioorg. Med. Chem. 1999; 7:105-117.

Kelso, et al. A Cyclic Metallopeptide Induces a Helicity in Short Peptide Fragments of Thermolysin. Angew. Chem. Int. Ed. 2003; 42(4):421-424.

Kelso, et al. α-Turn Mimetics: Short Peptide α-Helices Composed of Cyclic Metallopentapeptide Modules. J. Am. Chem. Soc. 2004;126:4828-4842.

Kemp, et al. Studies of N-Terminal Templates for α-Helix Formation. Synthesis and Conformational Analysis of Peptide Conjugates of (2S,5S,8S,11S)-1-Acetyl-1,4-diaza-3-keto-5-carboxy-10-thiatricyclo[2.8.1.04,8]-tridecane (Ac-Hel1-OH). J. Org. Chem. 1991; 56:6683-6697.

Kemp, et al. Studies of N-Terminal Templates for α-Helix Formation. Synthesis and Conformational Analysis of (2S,5S,8S,11S)-1-Acetyl-1,4-diaza-3-keto-5-carboxy-10-thiatricyclo[2.8.1.04,8]-tridecane (Ac-Hel1-OH). J. Org. Chem. 1991; 56:6672-6682.

Kielian, et al. Virus membrane-fusion proteins: more than one way to make a hairpin. Nat Rev Microbiol. Jan. 2006;4(1):67-76.

Kilby, et al. Potent Suppression of HIV-1 Replication in Humans by T-20, a Peptide Inhibitor of gp41-Mediated Virus Entry. Nat. Med. 1998; 4(11):1302-1307.

Kritzer, et al. Helical β-Peptide Inhibitors of the p53-hDM2 Interaction. J. Am. Chem. Soc. 2004; 126:9468-9469.

Kussie, et al. Structure of the MDM2 Oncoprotein Bound to the p53 Tumor Suppressor Transactivation Domain. Science. 1996; 274:948-953.

Kutzki, et al. Development of a Potent Bcl-xL Antagonist Based on α-Helix Mimicry, J. Am. Chem. Soc. 2002; 124:11838-11839.

Letai, et al. Distinct BH3 Domains Either Sensitize or Activate Mitochondrial Apoptosis, Serving as Prototype Cancer Therapeutics. Cancer Cell. 2002; 2:183-192.

Lifson, et al. On the Theory of Helix-coil Transition in Polypeptides. J. Chem. Phys. 1961; 34(6):1963-1974.

Litowski, et al. Designing Heterodimeric Two-stranded α-Helical Coiled-coils: Effects of Hydrophobicity and α-Helical Propensity on Protein Folding, Stability, and Specificity. J. Biol. Chem. 2002; 277(40):37272-37279.

(56) References Cited

OTHER PUBLICATIONS

Lyu, et al. Capping Interactions in Isolated α Helices: Position-dependent Substitution Effects and Structure of a Serine-capped Peptide Helix. Biochemistry. 1993; 32:421-425.
Lyu, et al. α-Helix Stabilization by Natural and Unnatural Amino Acids with Alkyl Side Chains. Proc. Nat'l Acad. Sci. USA. 1991; 88:5317-5320.
Marqusee, et al. Helix Stabilization by Glu—. . . Lys+ Salt Bridges in Short Peptides of De Novo Design. Proc. Nat'l Acad. Sci. USA. 1987; 84:8898-8902.
McNamara, et al. Peptides Constrained by an Aliphatic Linkage between Two Cα Sites: Design, Synthesis, and Unexpected Conformational Properties of an i,(i+4)-Linked Peptide J. Org. Chem. 2001; 66:4585-4594.
Miller, et al. oNBS-SPPS: A New Method for Solid-phase Peptide Synthesis. J. Am. Chem. Soc. 1998; 120:2690-2691.
Nelson, et al. Persistence of the α-Helix Stop Signal in the S-Peptide in Trifluoroethanol Solutions. Biochemistry. 1989; 28:5256-5261.
O'Neil, et al. A Thermodynamic Scale for the Helix-forming Tendencies of the Commonly Occurring Amino Acids. Science. 1990;250:646-651.
O'Shea, et al. Mechanism of Specificity in the Fos-Jun Oncoprotein Heterodimer. Cell. 1992; 68:699-708.
Ösapay, et al. Multicyclic Polypeptide Model Compounds. 2. Synthesis and Conformational Properties of a Highly α-Helical Uncosapeptide Constrained by Three Side-chain to Side-chain Lactam Bridges. J. Am. Chem. Soc. 1992; 114:6966-6973.
Pangborn, et al. Safe and Convenient Procedure for Solvent Purification. Organometallics. 1996; 15:1518-1520.
Petros, et al. Rationale for Bcl-xL/Bad Peptide Complex Formation from Structure, Mutagenesis, and Biophysical Studies. Protein Sci. 2000; 9:2528-2534.
Phelan et al., "A General Method for Constraining Short Peptides to an α-Helical Conformation," J. Am. Chem. Soc. 119(3):455-460 (1997).
Qian, et al. Helix-coil Theories: A Comparative Study for Finite Length Polypeptides J. Phys. Chem. 1992; 96:3987-3994.
Roehrl, et al. A General Framework for Development and Data Analysis of Competitive High-throughput Screens for Small-molecule Inhibitors of Protein—Protein Interactions by Fluorescence Polarization. Biochemistry. 2004; 43:16056-16066.
Roehrl, et al. Discovery of Small-molecule Inhibitors of the NFAT—Calcineurin Interaction by Competitive High-throughput Fluorescence Polarization Screening Biochemistry. 2004; 43:16067-16075.
Ruan, et al. Metal Ion Enhanced Helicity in Synthetic Peptides Containing Unnatural, Metal-ligating Residues. J. Am. Chem. Soc. 1990; 112:9403-9404.
Rutledge, et al. A View to a Kill: Ligands for Bcl-2 Family Proteins. Curr. Opin. Chem. Biol. 2002; 6:479-485.
Sattler, et al. Structure of Bcl-xL-Bak Peptide Complex: Recognition between Regulators of Apoptosis. Science. 1997; 275:983-986.
Schafmeister, et al. An All-hydrocarbon Cross-linking System for Enhancing the Helicity and Metabolic Stability of Peptides. J. Am. Chem. Soc. 2000; 122:5891-5892.
Shepherd, et al. Modular alpha-helical mimetics with antiviral activity against respiratory syncitial virus. J Am Chem Soc. Oct. 11, 2006;128(40):13284-9.
Shepherd, et al. Single Turn Peptide Alpha Helices with Exceptional Stability in Water. J. Am. Chem. Soc. 2005; 127:2974-2983.
Sia, et al. Short constrained peptides that inhibit HIV-1 entry. Proc Natl Acad Sci USA. Nov. 12, 2002;99(23):14664-9. Epub Nov. 4, 2002.
Stephens, et al. Inhibiting HIV fusion with a beta-peptide foldamer. J Am Chem Soc. Sep. 28, 2005;127(38):13126-7.
Still, et al. Rapid Chromatographic Technique for Preparative Separations with Moderate Resolution. J. Org. Chem. 1978; 43(14):2923-2925.
Trnka, et al. The Development of L2X2Ru=CHR Olefin Metathesis Catalysts: An Organometallic Success Story. Acc. Chem. Res. 2001; 34:18-29.

Turner, et al. Mitsunobu Glycosylation of Nitrobenzenesulfonamides: Novel Route to Amadori Rearrangement Products. Tetrahedron Lett. 1999; 40:7039-7042.
Tyndall, et al. Proteases Universally Recognize Beta Strands in Their Active Sites. Chem. Rev. 2005; 105:973-999.
Vassilev, et al. In Vivo Activation of the p53 Pathway by Small-molecule Antagonists of MDM2. Science. 2004; 303:844-848.
Walensky, et al. Activation of Apoptosis in Vivo by a Hydrocarbon-stapled BH3 Helix. Science. 2004; 305:1466-1470.
Wang et al., "Recognition of a Protein Receptor with the Hydrogen Bond Surrogate-based Artificial Alpha-helices," American Chemical Society Meeting, San Diego (Mar. 2005) (poster).
Wang et al., "Recognition of a Protein Receptor with the Hydrogen Bond Surrogate-based Artificial Alpha-helices," Chemical Biology Symposium, Hunter College (Jan. 2005) (poster).
Wang, et al. Enhanced metabolic stability and protein-binding properties of artificial alpha helices derived from a hydrogen-bond surrogate: application to Bcl-xL. Angew Chem Int Ed Engl. Oct. 14, 2005;44(40):6525-9.
Wang, et al. Evaluation of biologically relevant short alpha-helices stabilized by a main-chain hydrogen-bond surrogate. J Am Chem Soc. Jul. 19, 2006;128(28):9248-56.
Wild, et al. Peptides corresponding to a predictive alpha-helical domain of human immunodeficiency virus type 1 gp41 are potent inhibitors of virus infection. Proc Natl Acad Sci U S A. Oct. 11, 1994;91(21):9770-4.
Yang, et al. Synthesis and Helical Structure of Lactam Bridged BH3 Peptides Derived from Pro-apoptotic Bcl-2 Family Proteins. Bioorg. Med. Chem. Lett. 2004;14:1403-1406.
Yin, et al. Terphenyl-based Helical Mimetics That Disrupt the p53/HDM2 Interaction, Angew. Chem. Int. Ed. 2005; 44:2704-2707.
Zhang, et al. A cell-penetrating helical peptide as a potential HIV-1 inhibitor. J Mol Biol. May 2, 2008;378(3):565-80. Epub Mar. 6, 2008.
Zhang, et al. Development of a High-throughput Fluorescence Polarization Assay for Bcl-xL. Anal. Biochem. 2002; 307:70-75.
Zimm, et al. Theory of the Phase Transition between Helix and Random Coil in Polypeptide Chains. J. Chem. Phys. 1959; 31(2):526-535.
Wang, et al. Inhibition of HIV-1 fusion 1-15 by hydrogen-bond-surrogate-based alpha helices. Angewandte Chemie International Edition. 2008; 47(10):1879-1882.
Wang. Nucleation and stability of hydrogen-bond surrogate-derived alpha-helices and their applications in targeting protein-protein interactions. Dissertation, Department of Chemistry. New York University. 2007. 1-311.
U.S. Appl. No. 13/366,113, filed Feb. 3, 2012, Nash et al.
U.S. Appl. No. 13/370,057, filed Feb. 9, 2012, Nash et al.
International search report and written opinion dated Dec. 16, 2009 for PCT Application No. US08/88667.
Root, et al. Protein design of an HIV-1 entry inhibitor. Science. Feb. 2, 2001;291(5505):884-8.
U.S. Appl. No. 13/250,344, filed Sep. 30, 2011, Arora et al.
U.S. Appl. No. 13/252,751, filed Oct. 4, 2011, Walensky et al.
U.S. Appl. No. 13/680,905, filed Nov. 19, 2012, Verdine et al.
Office action dated Mar. 18, 2009 for U.S. Appl. No. 11/678,836.
Chan et al., "Evidence That a Prominent Cavity in the Coiled Coil of HIV Type 1 gp41 is an Attractive Drug Target," Proc. Nat'l Acad. Sci. U.S.A. 95:15613-17 (1998).
European Patent Application No. EP 08873198.9, Extended European Search Report (May 7, 2012).
International Application No. PCT/US2008/088667, International Preliminary Report on Patentability (Jul. 6, 2010).
Otaka et al., "Remodeling of gp41-C34 Peptide Leads to Highly Effective Inhibitors of the Fusion of HIV-1 With Target Cells," Angew. Chem. Int'l Ed. 41(16):2937-40 (2002).
Wang et al., "Nucleation and Stability of Hydrogen-Bond Surrogate-Based Alpha-Helices," Org. Biomol. Chem. 4 (22):4074-81 (2006).
Weissenhorn et al., "Atomic Structure of the Ectodomain From HIV-1 gp41," Nature 387:426-30 (1997).

* cited by examiner

Figures 1A-C

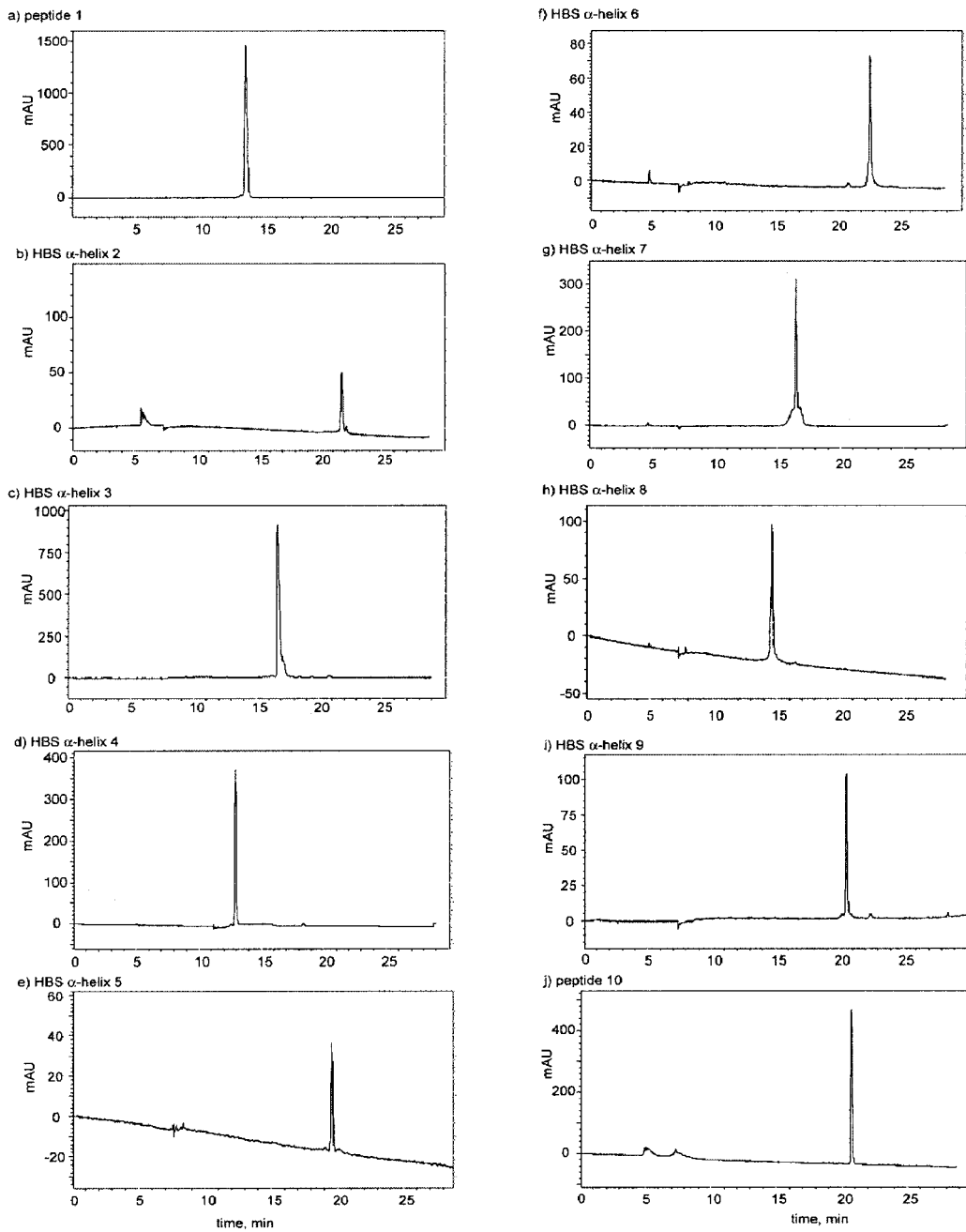
Figures 11A–J

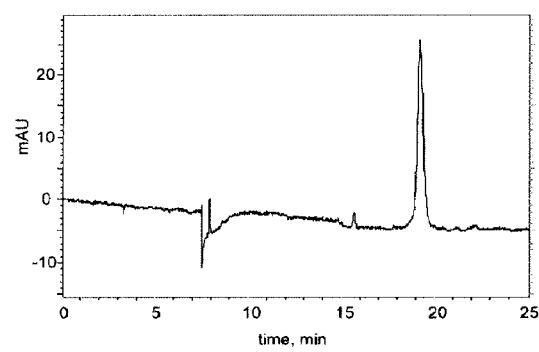
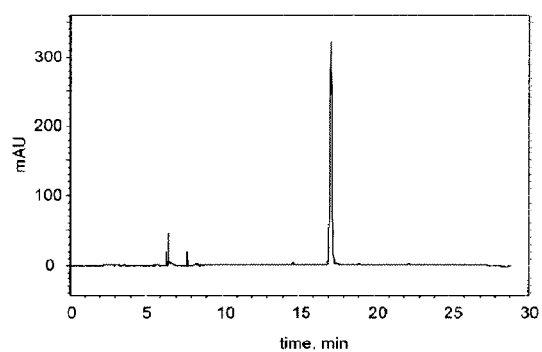
Figures 11K–L

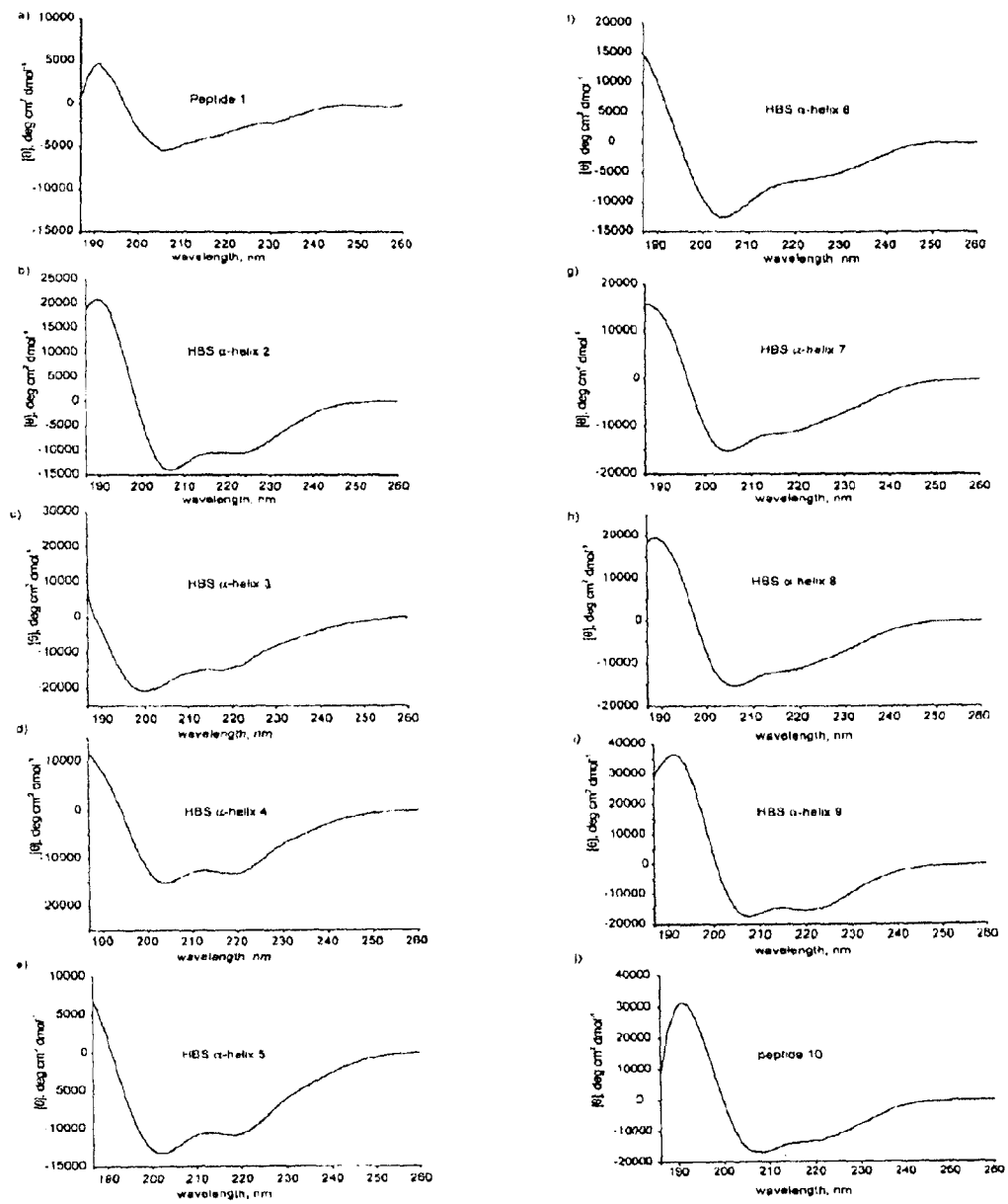
Figures 12A-J

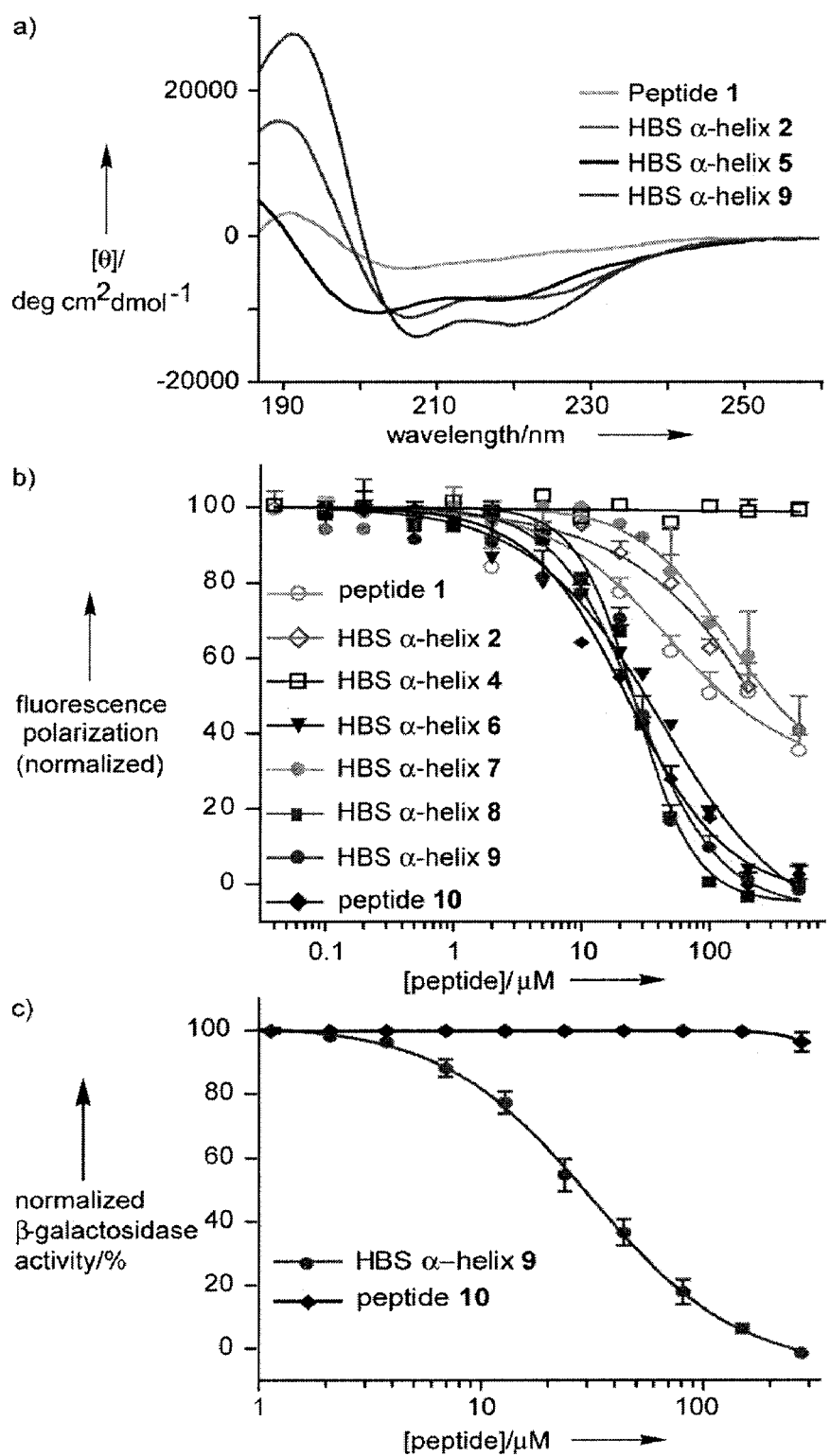
Figures 16A–C

CONTROL OF VIRAL-HOST MEMBRANE FUSION WITH HYDROGEN BOND SURROGATE-BASED ARTIFICIAL HELICES

CROSS-REFERENCE

This application claims the benefit of U.S. Provisional Application No. 61/018,118, filed Dec. 31, 2007, which application is incorporated herein by reference.

STATEMENT AS TO FEDERALLY SPONSORED RESEARCH

This invention was made with government support under grant numbers GM073943 and AI42382, both awarded by the National Institutes of Health. The government has certain rights in this invention.

BACKGROUND OF THE INVENTION

Enveloped viruses depend upon fusion between the viral membrane and a host cell membrane (the plasma membrane or an intracellular membrane, depending upon the specific virus) for delivery of viral genetic material to the host cell, thereby initiating infection of the host cell (Kielian & Ray, "Virus Membrane-fusion Proteins: More Than One Way to Make a Hairpin," *Nat. Rev.* 4:67-76 (2006), which is hereby incorporated by reference in its entirety). This membrane-fusion reaction relies on virus membrane-fusion proteins (Kielian & Ray, "Virus Membrane-fusion Proteins: More Than One Way to Make a Hairpin," *Nat. Rev.* 4:67-76 (2006), which is hereby incorporated by reference in its entirety). At least two classes of membrane-fusion proteins have been identified (Kielian & Ray, "Virus Membrane-fusion Proteins: More Than One Way to Make a Hairpin," *Nat. Rev.* 4:67-76 (2006), which is hereby incorporated by reference in its entirety). Class I fusion proteins contain two heptad repeat regions, termed the N-terminal heptad region and the C-terminal heptad region, between a hydrophobic "fusion peptide" region and a transmembrane domain (Dutch et al., "Virus Membrane Fusion Proteins: Biological Machines That Undergo a Metamorphosis," *Biosci. Rep.* 20(6):597-612 (2000), which is hereby incorporated by reference in its entirety). During membrane fusion, these heptad repeat regions ultimately adopt a highly stable coiled-coil assembly in which the N-terminal heptad repeat region forms an internal, trimeric coiled-coil buttressed by helices from the C-terminal heptad repeat region (Dutch et al., "Virus Membrane Fusion Proteins: Biological Machines That Undergo a Metamorphosis," *Biosci. Rep.* 20(6):597-612 (2000), which is hereby incorporated by reference in its entirety). Agents that interfere with the formation of this coiled-coil assembly can prevent viral-host cell membrane fusion, thereby inhibiting infection of the new host cell.

Viruses that use class I coiled-coil assemblies for viral infectivity include: Orthomyxoviridae, e.g., influenza virus (Dutch et al., "Virus Membrane Fusion Proteins: Biological Machines That Undergo a Metamorphosis," *Biosci. Rep.* 20(6):597-612 (2000); Kielian & Ray, "Virus Membrane-fusion Proteins: More Than One Way to Make a Hairpin," *Nat. Rev.* 4:67-76 (2006), which are hereby incorporated by reference in their entirety); Paramyxoviridae, e.g., Simian virus 5 (Dutch et al., "Virus Membrane Fusion Proteins: Biological Machines That Undergo a Metamorphosis," *Biosci. Rep.* 20(6):597-612 (2000); Kielian & Ray, "Virus Membrane-fusion Proteins: More Than One Way to Make a Hairpin," *Nat. Rev.* 4:67-76 (2006), which are hereby incorporated by reference in their entirety) and respiratory syncitial virus (Dutch et al., "Virus Membrane Fusion Proteins: Biological Machines That Undergo a Metamorphosis," *Biosci. Rep.* 20(6):597-612 (2000); Shepherd et al., "Modular α-Helical Mimetics with Antiviral Activity Against Respiratory Syncitial Virus," *J. Am. Chem. Soc.* 128:13284-9 (2006), which are hereby incorporated by reference in their entirety); Filoviridae, e.g., Ebola virus (Dutch et al., "Virus Membrane Fusion Proteins: Biological Machines That Undergo a Metamorphosis," *Biosci. Rep.* 20(6):597-612 (2000); Kielian & Ray, "Virus Membrane-fusion Proteins: More Than One Way to Make a Hairpin," *Nat. Rev.* 4:67-76 (2006), which are hereby incorporated by reference in their entirety); Retroviridae, e.g., Moloney murine leukemia virus, simian immunodeficiency virus, Human immunodeficiency virus ("HIV-1"), and human T cell leukemia virus (Dutch et al., "Virus Membrane Fusion Proteins: Biological Machines That Undergo a Metamorphosis," *Biosci. Rep.* 20(6):597-612 (2000); Kielian & Ray, "Virus Membrane-fusion Proteins: More Than One Way to Make a Hairpin," *Nat. Rev.* 4:67-76 (2006), which are hereby incorporated by reference in their entirety); Coronaviridae, e.g., Mouse hepatitis virus and SARS virus (Kielian & Ray, "Virus Membrane-fusion Proteins: More Than One Way to Make a Hairpin," *Nat. Rev.* 4:67-76 (2006), which is hereby incorporated by reference in its entirety); and Herpesviridae, e.g., human cytomegalovirus (English et al., "Rational Development of β-Peptide Inhibitors of Human Cytomegalovirus Entry," *J. Biol. Chem.* 281:2661-7 (2006), which is hereby incorporated by reference in its entirety).

HIV-1 is illustrative of viruses that use class I fusion proteins. HIV has been identified as the etiological agent responsible for acquired immune deficiency syndrome ("AIDS"), a fatal disease characterized by destruction of the immune system and the inability to fight off life threatening opportunistic infections. Recent statistics indicate that as many as 33 million people worldwide are infected with the virus (AIDS EPIDEMIC UPDATE at 1, United Nations Programme on HIV/AIDS (December 2007)). In addition to the large number of individuals already infected, the virus continues to spread. Estimates from 2007 point to close to 2.5 million new infections in that year alone (AIDS EPIDEMIC UPDATE at 1, United Nations Programme on HIV/AIDS (December 2007)). In the same year there were approximately 2.1 million deaths associated with HIV and AIDS (AIDS EPIDEMIC UPDATE at 1, United Nations Programme on HIV/AIDS (December 2007)).

Entry of HIV-1 into its target cells to establish an infection is mediated by viral envelope glycoprotein ("Env") and cell surface receptors (CD4 and a coreceptor, such as CXCR4 or CCR5) (Eckert & Kim, "Mechanisms of Viral Membrane Fusion and Its Inhibition," *Annu. Rev. Biochem.* 70:777-810 (2001), which is hereby incorporated by reference in its entirety). The mature Env complex is a trimer, with three gp120 glycoproteins associated non-covalently with three viral membrane-anchored gp41 subunits. Binding of gp120/gp41 to cellular receptors triggers a series of conformational changes in gp41 that ultimately leads to formation of a postfusion trimer-of-hairpins structure and membrane fusion (Chan et al., "Core Structure of gp41 from the HIV Envelope Glycoprotein," *Cell* 89:263-73 (1997); Weissenhorn et al., "Atomic Structure of the Ectodomain from HIV-1 gp41," *Nature* 387:426-30 (1997); Tan et al., "Atomic Structure of a Thermostable Subdomain of HIV-1 gp41," *Proc. Nat'l Acad. Sci. U.S.A.* 94:12303-8 (1997), which are hereby incorporated by reference in their entirety). As shown in FIGS. 1A and 1C, the core of the postfusion trimer-of-hairpins structure is a bundle of six α-helices: three N-peptide helices form an interior, parallel coiled-coil trimer, while three C-peptide helices pack in an antiparallel manner into hydrophobic grooves on the coiled-coil surface (Chan et al., "Core Structure of gp41 from the HIV Envelope Glycoprotein," *Cell* 89:263-73 (1997); Weissenhorn et al., "Atomic Structure of the Ectodomain from HIV-1 gp41," *Nature* 387:426-30 (1997); Tan et al., "Atomic Structure of a Thermostable Subdomain of HIV-1 gp41," *Proc. Nat'l Acad. Sci. U.S.A.* 94:12303-8 (1997), which are hereby incorporated by reference in their entirety). The N-peptide region features a hydrophobic pocket targeted by C-peptide residues W628, W631, and I635, as shown in FIG. 1B (Chan et al., "Evidence That a Prominent Cavity in the Coiled Coil of HIV Type 1 gp41 Is an Attractive Drug Target," *Proc. Nat'l Acad. Sci. U.S.A.* 95:15613-7 (1998), which is hereby incorporated by reference in its entirety). Agents that interfere with the formation of the gp41 coiled-coil hexamer are primary targets for vaccine and drug development (Deng et al., "Protein Design of a Bacterially Expressed HIV-1 gp41 Fusion Inhibitor,"*Biochem.* 46:4360-9 (2007), which is hereby incorporated by reference in its entirety). Peptides and synthetic molecules that bind to the N-terminal hydrophobic pocket and inhibit the formation of the six-helix bundle have been shown to effectively inhibit gp41-mediated HIV fusion (Wild et al., "Peptides Corresponding to a Predictive α-Helical Domain of Human Immunodeficiency Virus Type 1 gp41 Are Potent Inhibitors of Virus Infection," *Proc. Nat'l Acad. Sci. U.S.A.* 91:9770-4 (1994); Ferrer et al., "Selection of gp41-mediated HIV-1 Cell Entry Inhibitors from Biased Combinatorial Libraries of Non-natural Binding Elements," *Nat. Struct. Biol.* 6:953-60 (1999); Sia et al., "Short Constrained Peptides That Inhibit HIV-1 Entry," *Proc. Nat'l Acad. Sci. U.S.A.* 99:14664-9 (2002); Ernst et al., "Design of a Protein Surface Antagonist Based on α-Helix Mimicry: Inhibition of gp41 Assembly and Viral Fusion," *Angew. Chem. Int'l Ed. Engl.* 41:278-81 (2002), originally published at *Angew. Chem.* 114: 282-91 (2002); Frey et al., "Small Molecules That Bind the Inner Core of gp41 and Inhibit HIV Envelope-mediated Fusion," *Proc. Nat'l Acad. Sci. U.S.A.* 103:13938-43 (2006); Stephens et al., "Inhibiting HIV Fusion with a β-Peptide Foldamer," *J. Am. Chem. Soc.* 127:13126-7 (2005); Deng et al., "Protein Design of a Bacterially Expressed HIV-1 gp41 Fusion Inhibitor," *Biochem.* 46:4360-9 (2007), which are hereby incorporated by reference in their entirety).

However, not all patients are responsive to existing therapies, and the virus develops resistance to most, if not all, known agents. Thus, there is a need for new antiviral agents against HIV and other viruses that use class I fusion proteins.

SUMMARY OF THE INVENTION

A first aspect of the present invention relates to a peptide having one or more stable, internally-constrained hydrogen bond surrogate ("HBS") α-helices, where the peptide mimics at least a portion of a C-peptide helix or at least a portion of an N-peptide helix of a viral coiled-coil assembly. In one embodiment, the invention provides a peptide having a stable, internally-constrained alpha-helix, wherein said alpha helix is constrained by a crosslink formed by a carbon-carbon bond-forming reaction, and further wherein the peptide mimics at least a portion of a class I C-peptide helix or at least a portion of a class I N-peptide helix, and wherein the peptide is an inhibitor of viral infectivity. The carbon-carbon bond-forming reaction may be, for example, metathesis. In other embodiments, the class I C-peptide helix or the class I N-peptide helix is derived from a virus selected from the group of Orthomyxoviridae, Paramyxoviridae, Filoviridae, Retroviridae, Coronaviridae, Herpesviridae, influenza virus, Simian virus 5, respiratory syncitial virus, Ebola virus, Moloney murine leukemia virus, simian immunodeficiency virus, human immunodeficiency virus, human T cell leukemia virus, Mouse hepatitis virus, SARS virus, and human cytomegalovirus. For example, the virus is human immunodeficiency virus. Peptides of the invention may mimic at least a portion of a gp41 C-peptide helix or at least a portion of a gp41 N-peptide helix. In one embodiment, a peptide mimics at least a portion of a gp41 C-peptide helix, such as the WWI region of a gp41 C-peptide helix.

In another embodiment, a peptide of the invention or a peptide for use in a method of the invention comprises the formula:

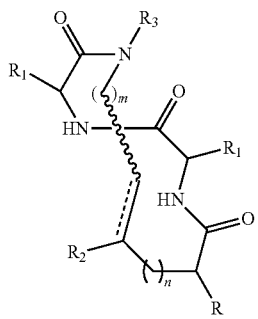

wherein
----- is a single or double carbon-carbon bond;
~~~ is a single bond and is cis or trans when ----- is a double bond;
n is 1 or 2;
m is zero or any positive integer;
R is hydrogen, an amino acid side chain, an alkyl group, or an aryl group;
$R_1$ is an amino acid side chain, an alkyl group, or an aryl group;
$R_2$ is an amino acid, second peptide, —OR, —$CH_2NH_2$, an alkyl group, an aryl group, hydrogen, or a group having a formula

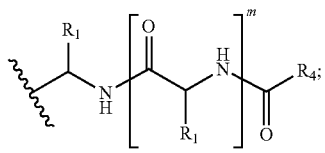

where $R_4$ is an amino acid, third peptide, —OR, —$NH_2$, an alkyl group, or an aryl group; and $R_3$ is a fourth peptide. $R_3$ may comprise, for example, the formula —WXXWXXX-IXXYXXXI—$R_4$, where X is any amino acid.

A peptide may comprise the amino acid sequence of SEQ ID NO: 9, and may have an internally-constrained alpha-helix spanning residues 1 through 4 of SEQ ID NO: 9. In other embodiments, the gp41 C-peptide helix has an amino acid sequence of SEQ ID NO: 11. Alternatively, a peptide mimics at least a portion of a gp41 N-peptide helix, such as the hydrophobic pocket of a gp41 N-peptide helix. The gp41 N-peptide helix may have, for example, an amino acid sequence of SEQ ID NO: 12.

The invention also provides pharmaceutical compositions comprising a peptide of the invention and a pharmaceutically acceptable vehicle.

In another aspect, the invention provides a method of inhibiting infectivity of a virus in a subject, the method comprising administering to the subject an effective amount of a composition comprising a peptide having a stable, internally-constrained alpha-helix, wherein said alpha helix is constrained by a crosslink formed by a carbon-carbon bond-forming reaction, and further wherein the peptide mimics at least a portion of a class I C-peptide helix or at least a portion of a class I N-peptide helix. The carbon-carbon bond-forming reaction may be, for example, metathesis. In some embodiments, the virus is selected from the group of Orthomyxoviridae, Paramyxoviridae, Filoviridae, Retroviridae, Coronaviridae, Herpesviridae, influenza virus, Simian virus 5, respiratory syncitial virus, Ebola virus, Moloney murine leukemia virus, simian immunodeficiency virus, human immunodeficiency virus, human T cell leukemia virus, Mouse hepatitis virus, SARS virus, and human cytomegalovirus.

In yet another aspect, the invention provides a method of synthesizing a peptide which is an inhibitor of viral infectivity comprising: selecting a precursor peptide comprising at least a portion of a class I C-peptide helix or at least a portion of a class I N-peptide helix; and promoting formation of a carbon-carbon bond, wherein said bond formation results in a stable, internally-constrained alpha-helix. Such bond formation may, for example, introduce a non-native carbon-carbon bond. In one embodiment, the bond formation is effected by metathesis. In some embodiments, the virus is human immunodeficiency virus and the peptide mimics at least a portion of a gp41 C-peptide helix or at least a portion of a gp41 N-peptide helix. For example, the peptide may comprise the formula WXXWXXXIXXYXXXI—$R_4$, where X is any amino acid and $R_4$ is an amino acid, third peptide, —OR, —$NH_2$, an alkyl group, or an aryl group. For example, the peptide may comprise the amino acid sequence of SEQ ID NO: 9, and has an internally-constrained alpha-helix spanning residues 1 through 4 of SEQ ID NO: 9. In another embodiment, the peptide comprises a gp41 C-peptide helix which has an amino acid sequence of SEQ. ID NO: 11.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates the HIV-1 gp41 core six-helix bundle. "N" denotes the N-peptide region; "C" denotes the C-peptide region. FIG. 1B shows the interaction of C-peptide residues W628, W631, and 1635 with the N-peptide (PDB code: 1AIK) (Chan et al., "Core Structure of gp41 from the HIV Envelope Glycoprotein," *Cell* 89:263-73 (1997), which is hereby incorporated by reference in its entirety). FIG. 1C is a helical wheel diagram showing interactions between C- and N-peptide coiled-coil domains. The sequence spanning residues 624-642 (SEQ ID NO: 1) of the C-peptide region is also shown.

FIGS. 11A-L are analytical HPLC plots for peptides 1-12. HPLC conditions: $C_{18}$ reversed phase column; 5% B to 15% B in 3 minutes, 15% B to 35% B in 20 minutes, 35% B to 100% B in 7 minutes; A: 0.1% aqueous TFA, B: acetonitrile; flow rate: 1.0 mL/min; monitored at 275 nm.

FIGS. 12A-J are CD spectra of peptides 1-10 in 10% TFE/PBS buffer.

FIGS. 16A-C are the circular dichroism spectra of 1, 2, 5, and 9 in 10% TFE in PBS buffer (FIG. 16A), a graph showing the determination of peptide binding to IZN17 by a fluorescence polarization assay (FIG. 16B), and a graph of the inhibition of gp41-mediated cell-cell fusion by HBS α-helix 9 and peptide 10 (FIG. 16C).

DETAILED DESCRIPTION OF THE INVENTION

Figure 1:
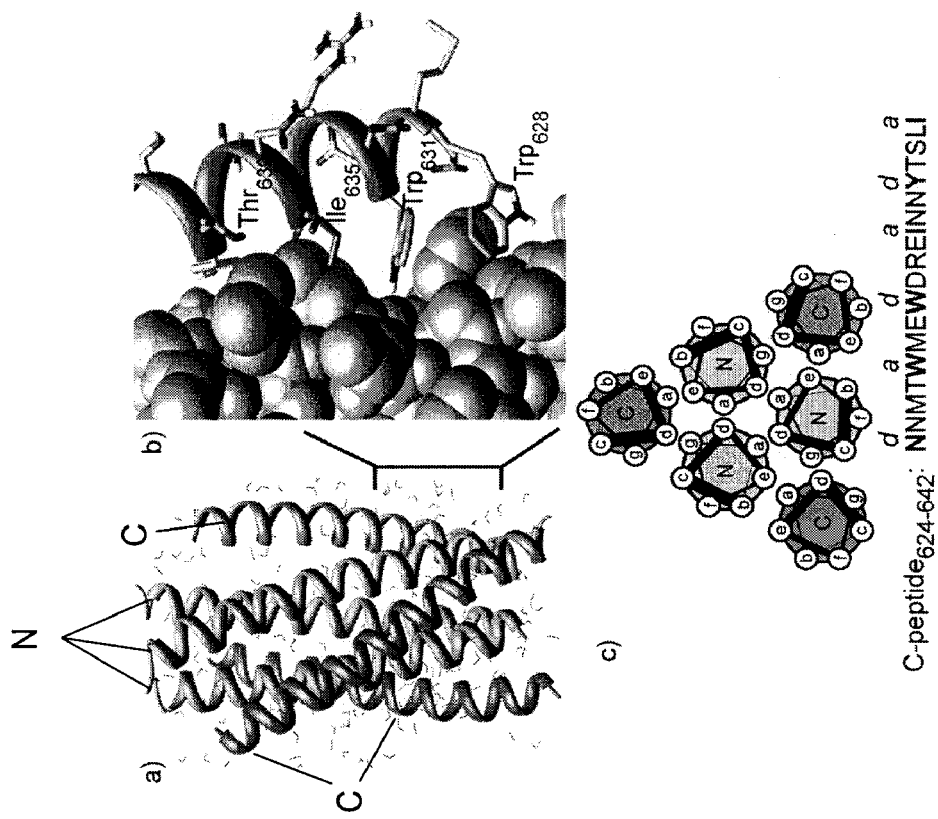
FIGS. 1A-C are schematic diagrams.

The present invention relates to hydrogen bond surrogate ("HBS")-derived α-helices that inhibit the formation of viral class I coiled-coil assemblies. These HBS helices can potentially function as in vivo inhibitors of class I fusion protein-protein interactions involved in viral infectivity.

A first aspect of the present invention relates to a peptide having one or more stable, internally-constrained HBS α-helices, where the peptide mimics at least a portion of a class I C-peptide helix or at least a portion of a class I N-peptide helix of a viral coiled-coil assembly.

A peptide of this aspect of the present invention may mimic at least a portion of a class I C-peptide helix or a class I N-peptide helix of a virus selected from the group of Orthomyxoviridae, Paramyxoviridae, Filoviridae, Retroviridae, Coronaviridae, Herpesviridae, influenza virus, Simian virus 5, respiratory syncitial virus, Ebola virus, Moloney murine leukemia virus, simian immunodeficiency virus, HIV-1, human T cell leukemia virus, Mouse hepatitis virus, SARS virus, and human cytomegalovirus.

In a preferred embodiment, the peptide according to this aspect of the present invention mimics at least a portion of an HIV-1 gp41 C-peptide helix or at least a portion of an HIV-1 gp41 N-peptide helix. These peptides are expected to interfere with the formation of the gp41 coiled-coil assembly, which is known to mediate HIV-1 entry into host cells.

Suitable peptides that mimic a portion of a gp41 C-peptide helix include peptides that mimic the WWI region of a gp41 C-peptide helix. This region interacts with a hydrophobic pocket on a corresponding N-peptide helix during formation of the coiled-coil hexamer. Thus, artificial α-helical mimics of this region are expected to competitively interfere with the native gp41 C-peptide helices for binding with this hydrophobic region. Similarly, suitable peptides that mimic a portion of a gp41 N-peptide helix include those that mimic a hydrophobic pocket of a gp41 N-peptide helix. These artificial α-helices are expected to competitively interfere with gp41 C peptide helices for binding with the native N-peptide helices.

By way of example, the artificial α-helices of the present invention can mimic at least a portion of the gp41 N-peptide and C-peptide helices shown in Table 1.

TABLE 1

Exemplary gp41 Helices.

| Domain Name | Sequence |
|---|---|
| gp41 C-peptide | HTTWMEWDREINNYTSLIHSLIEESQNQQEKNEQELLE (SEQ ID NO: 11) |
| gp41 N-peptide | QLLSGIVQQQNNLLRAIEAQQHLLQLTVWGIKQLQARILA (SEQ ID NO: 12) |

Generally, suitable peptides of the present invention include those that include the formula:

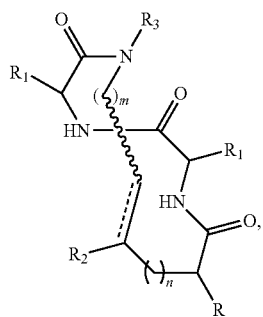

where
⁃⁃⁃⁃ is a single or double carbon-carbon bond;
∼∼∼ is a single bond and is cis or trans when ⁃⁃⁃⁃ is a double bond;
n is 1 or 2;
m is zero or any positive integer;
R is hydrogen, an amino acid side chain, an alkyl group, or an aryl group;
$R_1$ is an amino acid side chain, an alkyl group, or an aryl group;
$R_2$ is an amino acid, peptide, —OR, —$CH_2NH_2$, an alkyl group, an aryl group, hydrogen, or a group having a formula

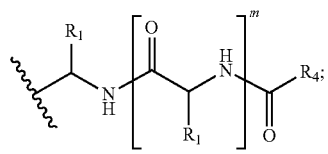

where $R_4$ is an amino acid, peptide, —OR, —$NH_2$, an alkyl group, or an aryl group and R3 is a fourth peptide.

In some embodiments, $R_3$ is a peptide comprising the formula —WXXWXXXIXXYXXXI (SEQ ID NO: 13)-$R_4$, where X is any amino acid. In another embodiment, a peptide of the present invention includes the amino acid sequence of SEQ ID NO: 9, and has an internally-constrained α-helical region spanning residues 1 through 4 of SEQ ID NO: 9.

As will be apparent to one of ordinary skill in the art, the methods of the present invention may be used to prepare peptides having highly stabilized, internally-constrained α-helices. The constraint may be placed anywhere within the peptide, not just at the N-terminus. For example, a compound prepared according to the methods of the present invention may have the formula

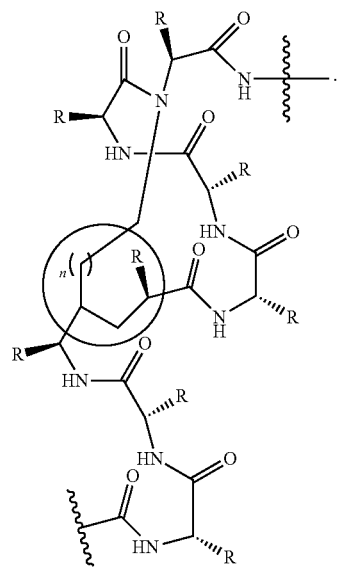

constraint in the middle
n = 1, 2

The peptides produced according to the methods of the present invention may, for example, be less than 15 amino acids, including, for example, less than 10 amino acid residues.

The present invention also relates to peptides having one or more stable, internally-constrained α-helices. The one or more stable, internally-constrained secondary structures includes the following motifs:

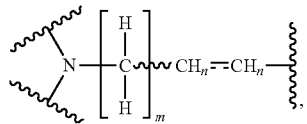

-continued

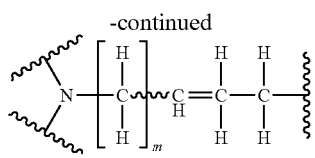

where ---- is a single or double bond, ∿∿ is a single bond and is cis or trans when ---- is a double bond; n is 1 or 2; and m is any number. Examples of such motifs include:

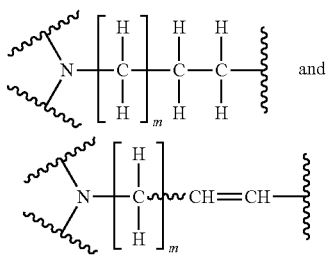

Figure 2:
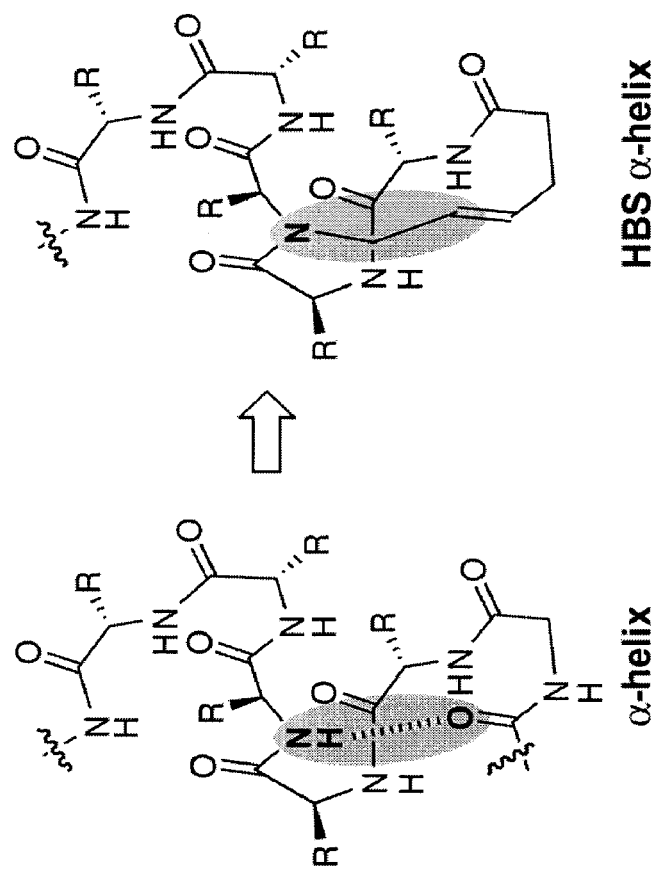
FIG. 2 is a schematic diagram illustrating the HBS approach. HBS α-helices feature a carbon-carbon bond in place of an i and i+4 hydrogen bond. R=amino acid side chain.
Figure 3:
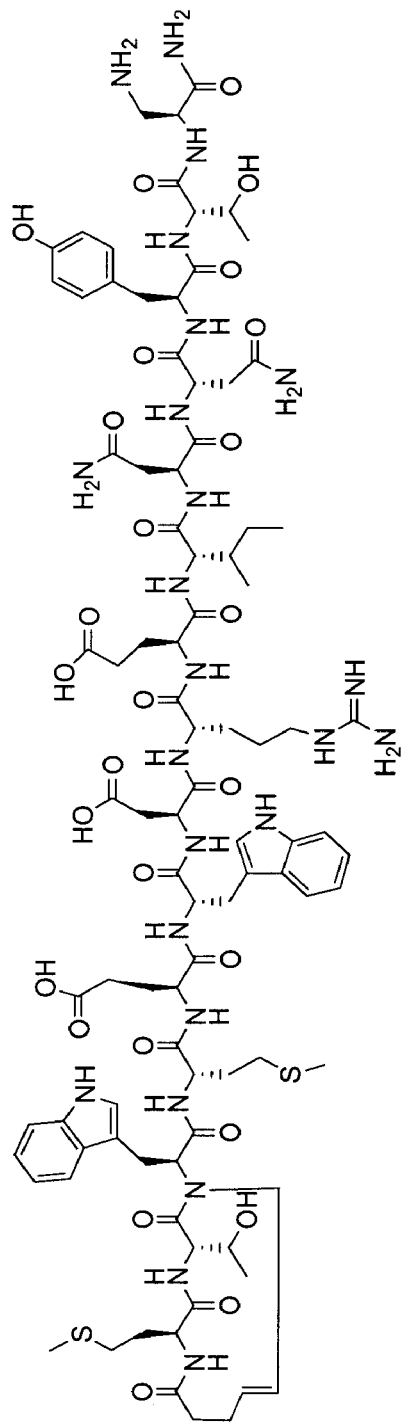
FIG. 3 is a schematic diagram of HBS α-helix 2, which has an amino acid sequence of XMTWMEWDREINNYT (SEQ ID NO: 2, where X is a pentenoic acid residue).
Figure 4:
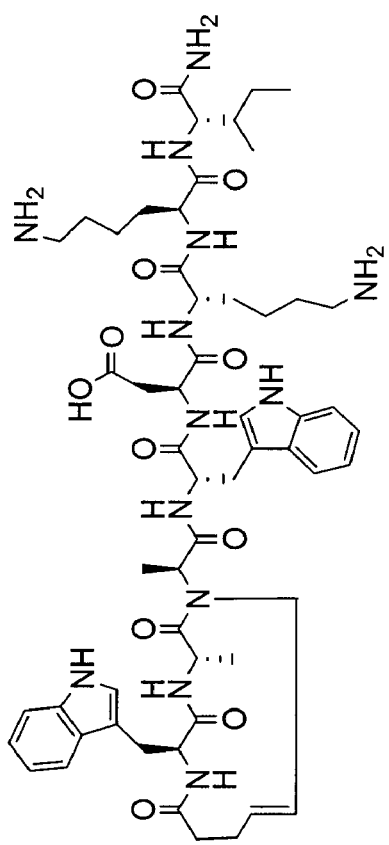
FIG. 4 is a schematic diagram of HBS α-helix 3, which has an amino acid sequence of XWAAWDKKI (SEQ ID NO: 3, where X is a pentenoic acid residue).
Figure 5:
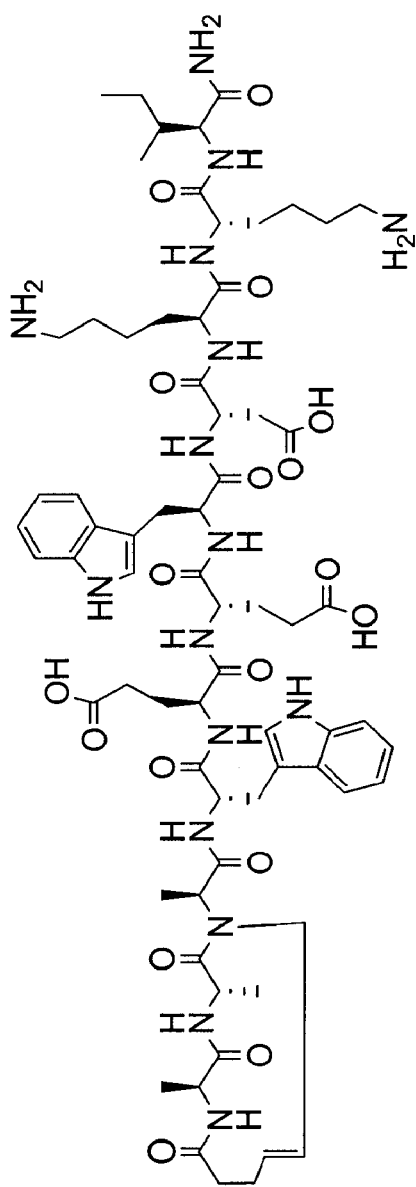
FIG. 5 is a schematic diagram of HBS α-helix 4, which has an amino acid sequence of XAAAWEEWDKKI (SEQ ID NO: 4, where X is a pentenoic acid residue).
Figure 6:
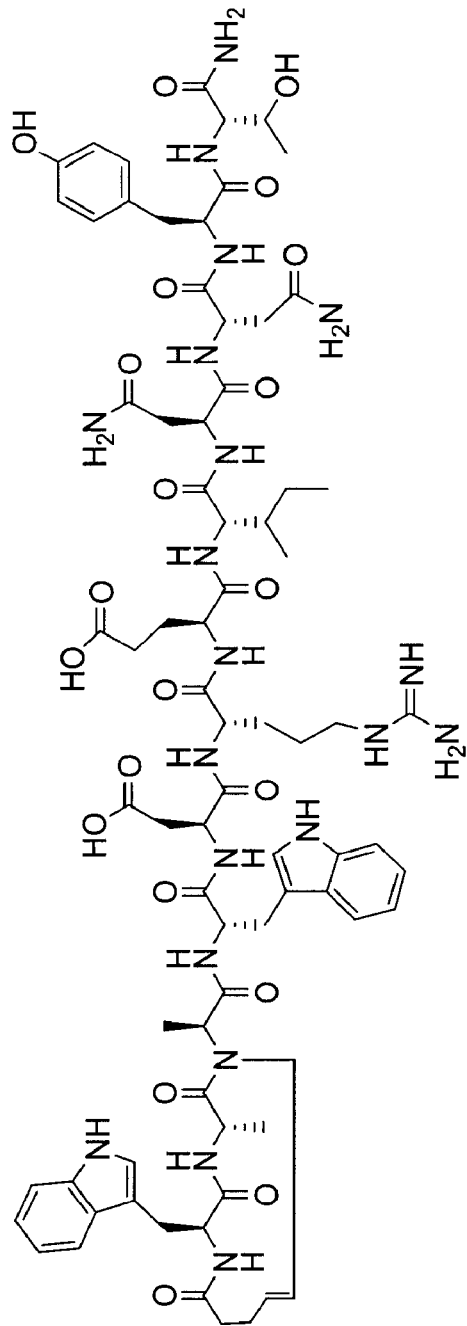
FIG. 6 is a schematic diagram of FIBS α-helix 5, which has an amino acid sequence of XWAAWDREINNYT (SEQ ID NO: 5, where X is a pentenoic acid residue).
Figure 7:
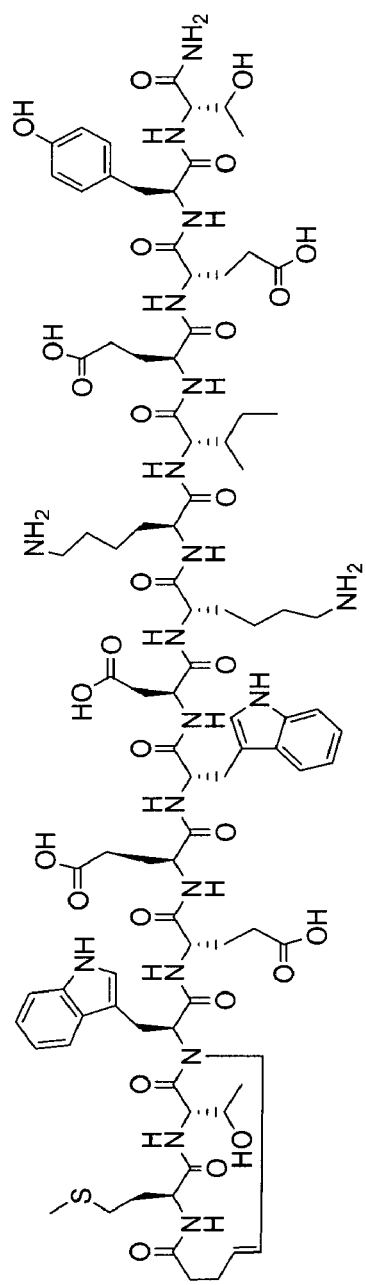
FIG. 7 is a schematic diagram of HBS α-helix 6, which has an amino acid sequence of XMTWEEWDKKIEEYT (SEQ ID NO: 6, where X is a pentenoic acid residue).
Figure 8:
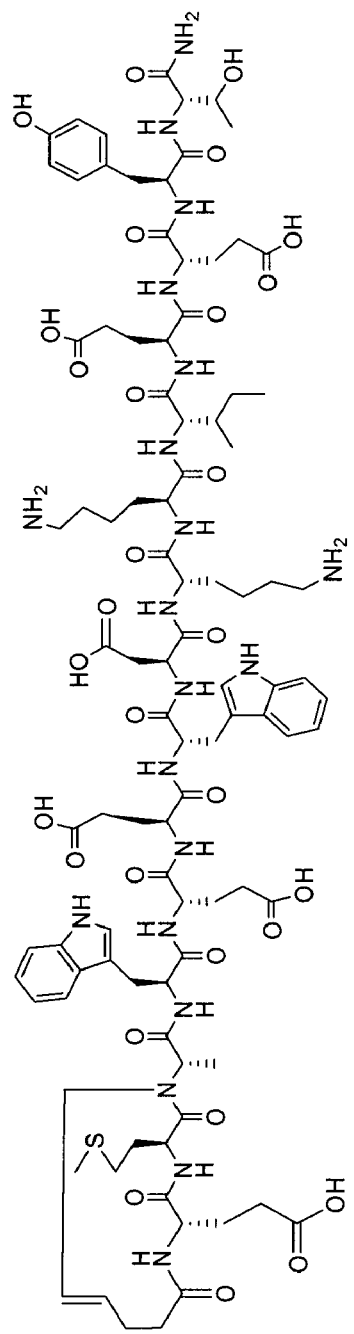
FIG. 8 is a schematic diagram of FIBS α-helix 7, which has an amino acid sequence of XEMAWEEWDKKIEEYT (SEQ ID NO: 7, where X is a pentenoic acid residue).
Figure 9:
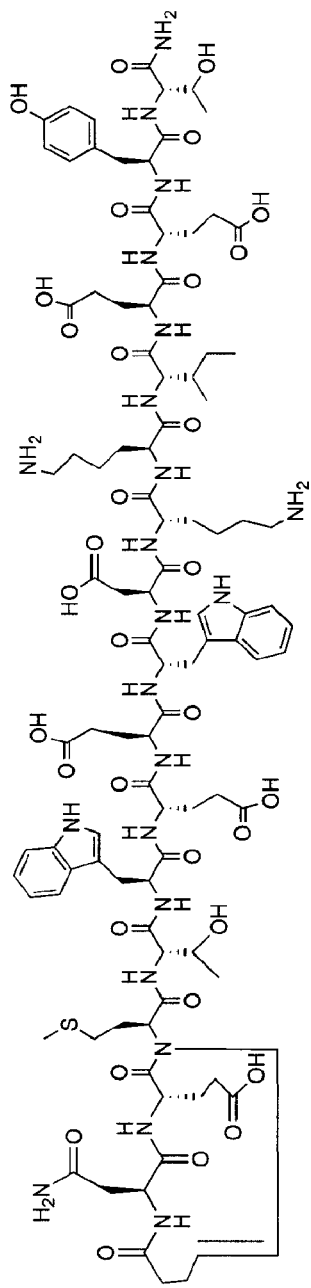
FIG. 9 is a schematic diagram of HBS α-helix 8, which has an amino acid sequence of XNEMTWEEWDKKIEEYT (SEQ ID NO: 8, where X is a pentenoic acid residue).
Figure 10:
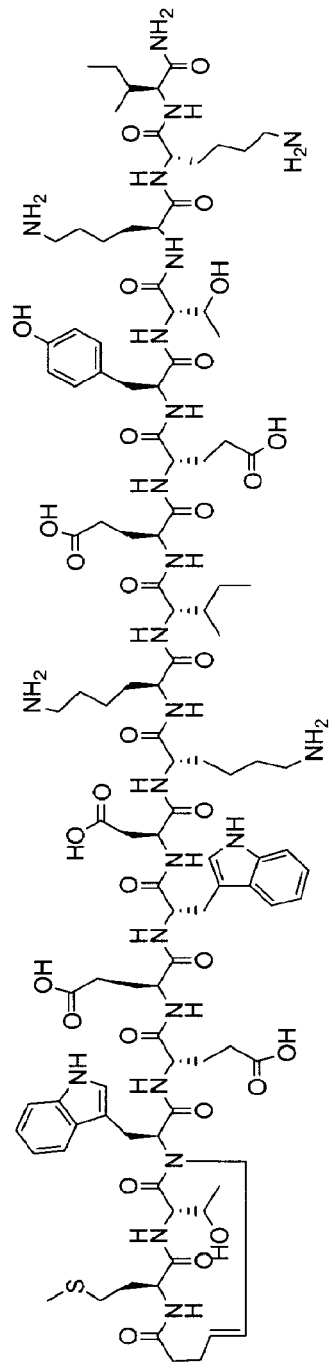
FIG. 10 is a schematic diagram of FIBS α-helix 9, which has an amino acid sequence of XMTWEEWDKKIEEYTKKI (SEQ ID NO: 9, where X is a pentenoic acid residue).

HBS α-helices of the present invention are obtained by replacing an N-terminal main-chain i and i+4 hydrogen bond with a carbon-carbon bond through a ring-closing metathesis reaction, as shown in FIG. 2 (U.S. Pat. No. 7,202,332 to Arora et al.; Chapman & Arora, "Optimized Synthesis of Hydrogen-bond Surrogate Helices: Surprising Effects of Microwave Heating on the Activity of Grubbs Catalysts," *Org. Lett.* 8:5825-8 (2006); Chapman et al., "A Highly Stable Short α-Helix Constrained by a Main-chain Hydrogen-bond Surrogate," *J. Am. Chem. Soc.* 126:12252-3 (2004); Dimartino et al., "Solid-phase Synthesis of Hydrogen-bond Surrogate-derived α-Helices," *Org. Lett.* 7:2389-92 (2005), which are hereby incorporated by reference in their entirety). The hydrogen bond surrogate pre-organizes an α-turn and stabilizes the peptide sequence in an α-helical conformation. HBS α-helices have been shown to adopt stable α-helical conformations from a variety of short peptide sequences (Wang et al., "Evaluation of Biologically Relevant Short α-Helices Stabilized by a Main-chain Hydrogen-bond Surrogate," *J. Am. Chem. Soc.* 128:9248-56 (2006), which is hereby incorporated by reference in its entirety). It has also been shown that these artificial α-helices can target their expected protein receptor with high affinity (Wang et al., "Enhanced Metabolic Stability and Protein-binding Properties of Artificial α Helices Derived from a Hydrogen-bond Surrogate: Application to Bcl-xL," *Angew. Chem. Int'l Ed. Engl.* 44:6525-9 (2005), originally published at *Angew. Chem.* 117:6683-7 (2005), which is hereby incorporated by reference in its entirety).

In another aspect, preparing a compound of the invention involves providing a peptide precursor compound and promoting carbon-carbon bond formation to result in a stable, internally-constrained alpha-helix.

In one embodiment, the precursor has the formula:

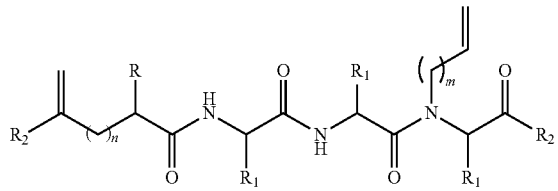

The compound of the formula above may be reacted under conditions effective to promote formation of a carbon-carbon bond. Such a reaction may be, for example, metathesis. The exceptional functional group tolerance displayed by the olefin metathesis catalysts for the facile introduction of non-native carbon-carbon constraints in the preparation of peptidomimetics suggests that X and Y could be two carbon atoms connected through an olefin metathesis reaction, as shown in Scheme 2 (Hoveyda et al., "Ru Complexes Bearing Bidentate Carbenes: From Innocent Curiosity to Uniquely Effective Catalysts for Olefin Metathesis," *Org. Biomolec. Chem.* 2:8-23 (2004); Trnka et al., "The Development of L2X2Tu=CHR Olefin Metathesis Catalysts: An Organometallic Success Story," *Accounts Chem. Res.* 34:18-29 (2001), which are hereby incorporated by reference in their entirety).

This aspect of the present invention may, for example, involve a ring-closing olefin metathesis reaction. An olefin metathesis reaction couples two double bonds (olefins) to afford two new double bonds (one of which is typically ethylene gas). A ring-closing olefin metathesis utilizes an olefin metathesis reaction to form a macrocycle. In this reaction, two double bonds within a chain are connected. The reaction may be performed with a metathesis catalyst, for example of the formula

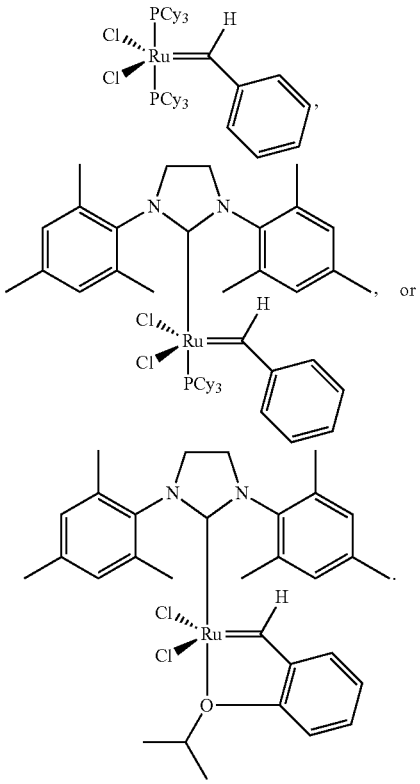

In other embodiments, the metathesis catalyst is of the formula

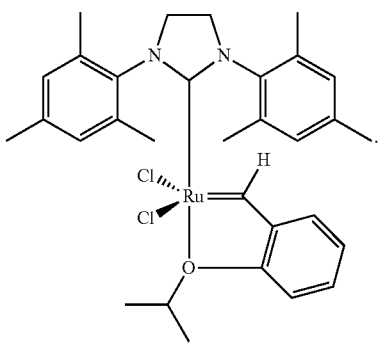

The metathesis reaction may be performed, for example, at a temperature between about 25° C. and 110° C., and more preferably, at a temperature of about 50° C.

The metathesis reaction may be performed with an organic solvent, such as dichloromethane, dichloroethane, trichloroethane, or toluene.

The reactions disclosed herein may, for example, be carried out on a solid support. Suitable solid supports include particles, strands, precipitates, gels, sheets, tubing, spheres, containers, capillaries, pads, slices, films, plates, slides, discs, membranes, etc. These solid supports can be made from a wide variety of materials, including polymers, plastics, ceramics, polysaccharides, silica or silica-based materials, carbon, metals, inorganic glasses, membranes, or composites thereof. The substrate is preferably flat but may take on a variety of alternative surface configurations. For example, the substrate may contain raised or depressed regions on which the synthesis takes place. The substrate and its surface preferably form a rigid support on which to carry out the reactions described herein. Other substrate materials will be readily apparent to those of ordinary skill in the art upon review of this disclosure.

The metathesis reaction performed may initially yield a compound in which the newly formed carbon-carbon bond is a double bond. This double bond can be subsequently converted to a single bond by hydrogenation methods known in the art.

A second aspect of the present invention relates to a method of inhibiting viral infectivity of a subject. This method involves administering to the subject an effective amount of a composition that includes a peptide of the present invention that mimics at least a portion of a class O N- or C-peptide helix. In a preferred embodiment, the method of this aspect of the present invention inhibits HIV infectivity of a subject. In this embodiment, the composition includes a peptide of the present invention that mimics a gp41 N-peptide helix or gp41 C-peptide helix.

Inhibiting infectivity according to this aspect of the present invention refers to any decrease in the rate and/or degree of transmission of the virus. This includes, without limitation, inhibiting transmission of the virus from one individual to another, as well as inhibiting further transmission of the virus within an infected individual.

The composition may be administered to individuals already infected with the virus (to inhibit transmission of the virus to others, and/or to inhibit further transmission of the virus within the infected individual), as well as to individuals not already infected with the virus (to inhibit transmission of the virus to the individual).

As will be apparent to one of ordinary skill in the art, administering may be carried out using generally known methods.

Administration can be accomplished either via systemic administration to the subject or via targeted administration to affected cells. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, by application to mucous membranes (such as that of the nose, throat, bronchial tubes, genitals, and/or anus), or implantation of a sustained release vehicle.

Typically, the peptide of the present invention will be administered to a mammal as a pharmaceutical formulation that includes the therapeutic agent and any pharmaceutically acceptable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers and/or excipients. The amount of active compound in such therapeutically useful compositions is such that a suitable dosage unit will be obtained.

The agents may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The agents may also be administered parenterally. Solutions or suspensions of the agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The agents of the present invention may be administered directly to a targeted tissue, e.g., tissue that is susceptible to infection by the virus. Additionally and/or alternatively, the agent may be administered to a non-targeted area along with one or more agents that facilitate migration of the agent to (and/or uptake by) a targeted tissue, organ, or cell. While the targeted tissue can be any tissue subject to infection by the virus, preferred target tissues in the case of inhibiting HIV-1 infection include mucous membranes of the mouth, genitals, and rectum. As will be apparent to one of ordinary skill in the art, the therapeutic agent itself be modified to facilitate its transport to (and uptake by) the desired tissue, organ, or cell.

Exemplary delivery devices include, without limitation, nebulizers, atomizers, liposomes, transdermal patches, implants, implantable or injectable protein depot compositions, and syringes. Other delivery systems which are known to those of skill in the art can also be employed to achieve the desired delivery of the therapeutic agent to the desired organ, tissue, or cells in vivo to effect this aspect of the present invention.

Any suitable approach for delivery of the agents can be utilized to practice this aspect of the present invention. Typically, the agent will be administered to a patient in a vehicle that delivers the agent(s) to the target cell, tissue, or organ.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., each of which is hereby incorporated by reference in its entirety.

These liposomes can be produced such that they contain, in addition to the therapeutic agents of the present invention, other therapeutic agents, such as anti-inflammatory agents, which would then be released at the target site (e.g., Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), which is hereby incorporated by reference in its entirety).

An alternative approach for delivery of proteins or polypeptide agents (e.g., peptides of the present invention) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., the artificial α-helix of the present invention). The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein.

Administration can be carried out as frequently as required and for a duration that is suitable to provide effective treatment against viral infection. For example, administration can be carried out with a single sustained-release dosage formulation or with multiple daily doses. Administration can be carried out before, concurrently with, and/or after exposure of the subject to the virus.

The amount to be administered will, of course, vary depending upon the treatment regimen. Generally, an agent is administered to achieve an amount effective for a reduction in infectivity of the virus (i.e., a therapeutically effective amount). Thus, a therapeutically effective amount can be an amount which is capable of at least partially preventing transmission of the virus to the subject, or spread of the virus within the subject. The dose required to obtain an effective amount may vary depending on the agent, formulation, virus, and individual to whom the agent is administered.

Determination of effective amounts may also involve in vitro assays in which varying doses of agent are administered to cells in culture and the concentration of agent effective for inhibiting infectivity is determined in order to calculate the concentration required in vivo. Effective amounts may also be based on in vivo animal studies. A therapeutically effective amount can be determined empirically by those of skill in the art.

EXAMPLES

Example 1

Synthesis of Peptides 1-11 and Characterization of Peptides 1-12

Peptides 1-11 were synthesized as shown in Scheme 1. Peptides 1 (i.e., AcMTWMEWDREINNYT-NH$_2$ (SEQ ID NO: 14)), 10 (i.e., AcMTWEEWDKKIEEYTKKI—NH$_2$ (SEQ ID NO: 15)), and 11 (i.e., peptide IZN17, AcIKKEIEAIKKEQEAIKKKIEAIEK-LLQLTVWGIKQLQARIL-NH$_2$ (SEQ ID NO: 16)), and resin-bound bis-olefins (17) were synthesized by conventional Fmoc solid phase chemistry on Rink amide HMBA resin (NovaBiochem), 0.05-0.15 mmol scale, with appropriate substitutions of N(allyl)-dipeptides 13-16 and 4-pentenoic acid. In each coupling step, the Fmoc group was removed by treatment with 20% piperidine in NMP (2×20 min). The next Fmoc amino acid (4 equiv.) in the sequence was activated with HBTU (3.6 equiv.) in a 5% DIPEA/NMP solution for 15 minutes, added to the resin bearing the free amine. The resulting mixture was shaken for 60 minutes. The coupling efficiency for each step was monitored by ninhydrin test. After the peptide was assembled on the resin, the resin was thoroughly washed with DMF, methanol, and dichloromethane, respectively, and dried under vacuum overnight.

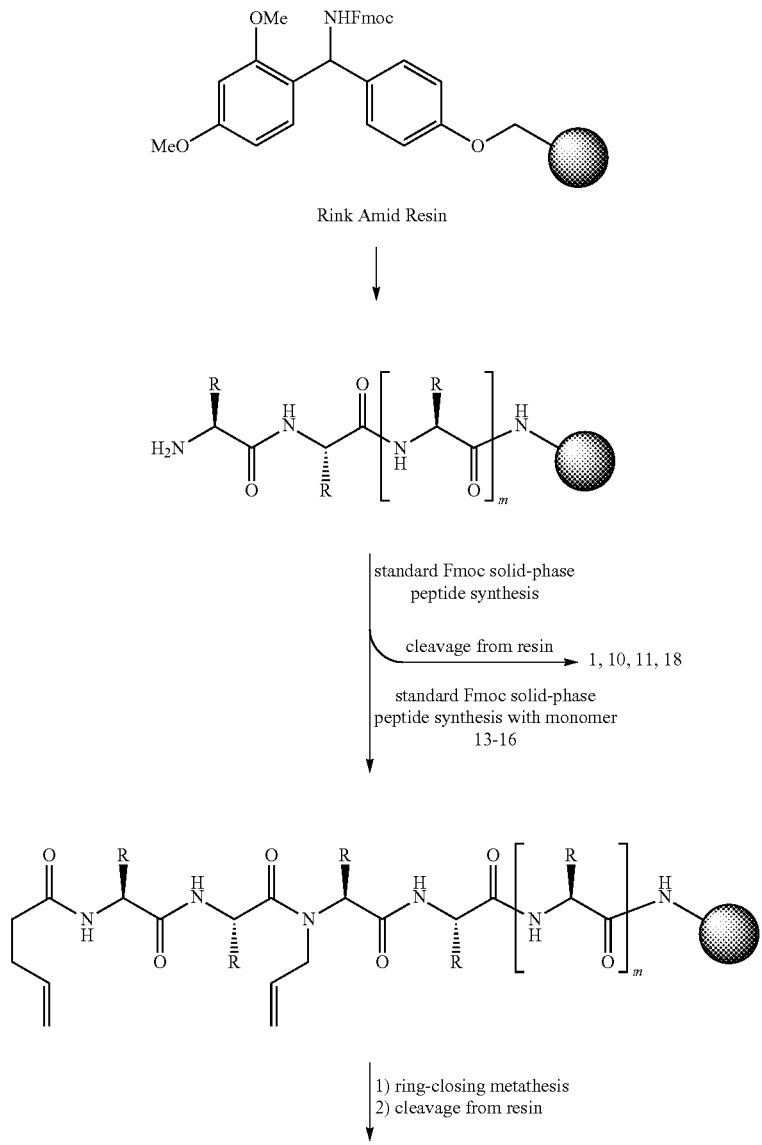

Scheme 1. Synthesis of Peptides 1-10

HBS α-helices 2-9

-continued

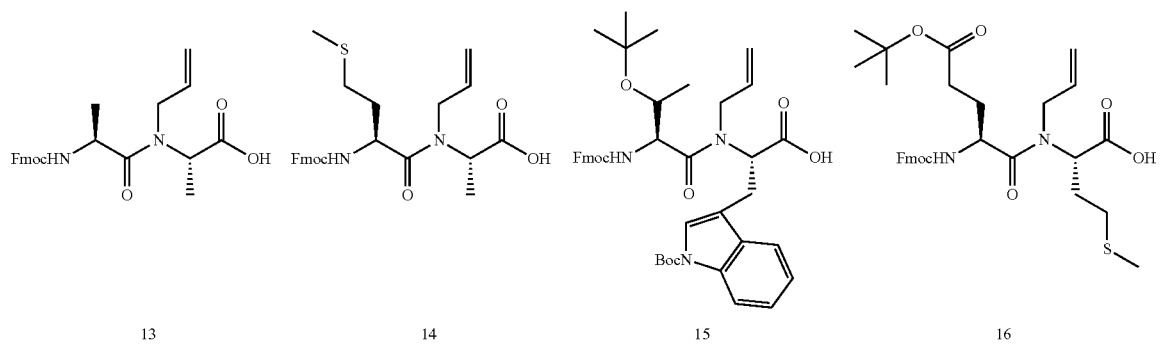

13   14   15   16

Microwave-assisted ring-closing metathesis reactions on resin-bound bis-olefins (17) were performed with the Hoveyda-Grubbs catalyst (0.15 equiv.) in dichloroethane as described in Chapman & Arora, "Optimized Synthesis of Hydrogen-bond Surrogate Helices: Surprising Effects of Microwave Heating on the Activity of Grubbs Catalysts," Org. Lett. 8:5825-8 (2006), which is hereby incorporated by reference in its entirety. The reaction mixture was irradiated with these settings: 250 W maximum power, 120° C., 5 minute ramp time, and 10 minute hold time. Resin bound peptides were cleaved from the resin by treatment with a cleavage cocktail ($CF_3CO_2H:H_2O$:triisopropylsilane, 95:2.5:2.5) for 1.5 hours, and purified by reversed-phase HPLC to afford HBS α-helices 2-9, which are shown in FIGS. 3-10. HPLC plots for peptides 1-12 are shown in FIGS. 11A-L.

Peptides 1-12 were examined using liquid chromatography-mass spectrometry ("LCMS"). LCMS data were obtained on an Agilent 1100 series. The LCMS results are shown in Table 2.

TABLE 2

Mass spectrometry results for Peptides 1-12 (LC/MSD (XCT) electrospray trap).

| peptide | Expected [M + H]+ | Found [M + H]+ |
|---------|-------------------|----------------|
| 1  | 1929.8 | 1929.6 |
| 2  | 2068.0 | 2068.6 |
| 3  | 1110.6 | 1111.1 |
| 4  | 1439.7 | 1440.5 |
| 5  | 1631.8 | 1632.2 |
| 6  | 1981.0 | 1981.8 |
| 7  | 2080.0 | 2080.0 |
| 8  | 2224.0 | 2225.0 |
| 9  | 2350.2 | 2351.2 |
| 10 | 2298.2 | 2299.0 |
| 11 | 2478.0 | 2478.6 |
| 12 | 4855.9 | 4854.7 |

Example 2

Circular Dichroism Spectroscopy of Peptides 1-10

CD spectra were recorded on an AVIV 202SF CD spectrometer equipped with a temperature controller using 1 mm length cells and a scan speed of 5 nm/min. The spectra were averaged over 10 scans with the baseline subtracted from analogous conditions as that for the samples. The samples were prepared in 0.1× phosphate buffered saline (13.7 mM NaCl, 1 mM phosphate, 0.27 mM KCl, pH 7.4), containing 10% trifluoroethanol, with the final peptide concentration of 50-100 μM. The concentrations of unfolded peptides were determined by the UV absorption of the tyrosine residue at 276 nm in 6.0 M guanidinium hydrochloride aqueous solution. The helix content of each peptide was determined from the mean residue CD at 222 nm, $[\theta]_{222}$ (deg $cm^2$ $dmol^{-1}$) corrected for the number of amino acids. Percent helicity was calculated from the ratio $[\theta]_{222}/[\theta]_{max}$, where $[\theta]_{max}=(-44000+250T)(1-k/n)$, with k=4.0 and n=number of residues. For details on $\theta_{max}$ calculations for HBS helices, see Wang et al., "Evaluation of Biologically Relevant Short α-Helices Stabilized by a Main-chain Hydrogen-bond Surrogate," J. Am. Chem. Soc. 128:9248-56 (2006), which is hereby incorporated by reference in its entirety. The CD spectra for peptides 1-10 are shown in FIGS. 12A-J.

Example 3

Affinity of Peptide 12 for IZN17

Figure 13:
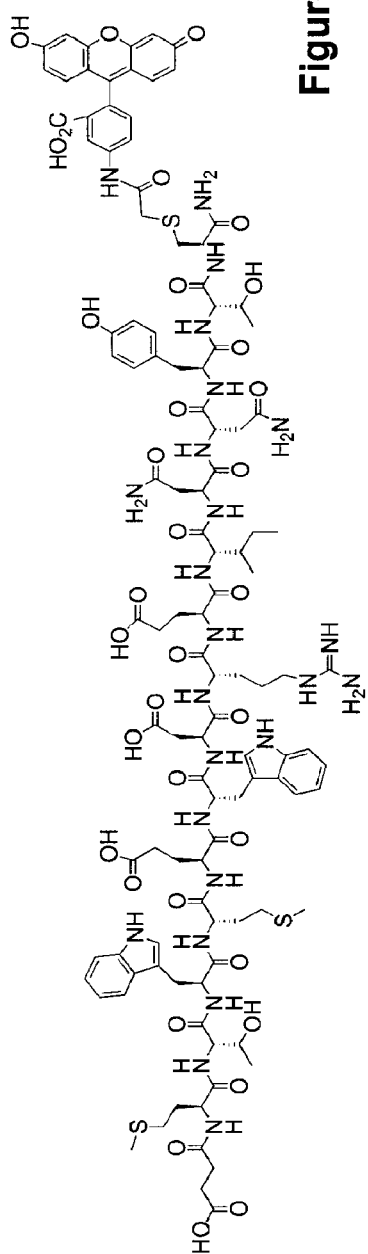
FIG. 13 is a schematic diagram of peptide 12 (i.e., Suc-MTWMEWDERINNYTC$^{Flu}$-$NH_2$ (SEQ ID NO: 10)).
Figure 14:
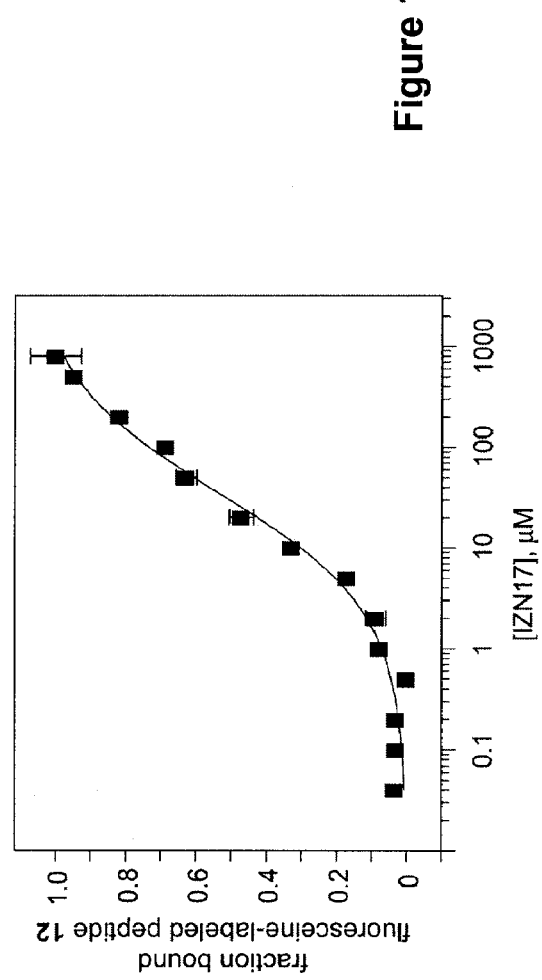
FIG. 14 is a graph showing the saturation binding curve of fluorescein-labeled peptide 12 with IZN17 in PBS buffer at 25° C.

The relative affinity of peptides 1-10 for IZN17 (i.e., peptide 11) was determined using a fluorescence polarization-based competitive binding assay (Eckert & Kim, "Design of Potent Inhibitors of HIV-1 Entry from the gp41 N-Peptide Region," Proc. Nat'l Acad. Sci. U.S.A. 98:11187-92 (2001); Stephens et al., "Inhibiting HIV Fusion with a β-Peptide Foldamer," J. Am. Chem. Soc. 127:13126-7 (2005), which are hereby incorporated by reference in their entirety) with fluorescein-labeled peptide 12, shown in FIG. 13. FIG. 14 is a graph showing the saturation binding curve of fluorescein-labeled peptide 12 with IZN17 in PBS buffer at 25° C.

All samples were prepared in 96-well plates in 1× phosphate buffered saline (137 mM NaCl, 10 mM phosphate, 2.7 mM KCl, pH 7.4) with 0.1% pluronic F-68 (Sigma). A solution of 25 μM IZN17 and 15 nM fluorescein-labeled peptide 12 was incubated at 25° C. After 1 hour, appropriate concentrations (10 nM to 500 μM) of the antagonists (peptides 1-10) were added. The total volume of the incubation solution was 60 μL. After 1 hour, the amount of dissociated fluorescent probe 12 was determined using a DTX 880 Multimode Detector (Beckman) at 25° C., with excitation and emission wavelengths of 485 and 525 nm, respectively.

The binding affinity ($K_D$) values reported 3 sec Example 6) for each peptide are the averages of 3~5 individual measurements, and were determined by fitting the experimental data to a sigmoidal dose-response nonlinear regression model on GraphPad Prism 4.0.

Figure 15:
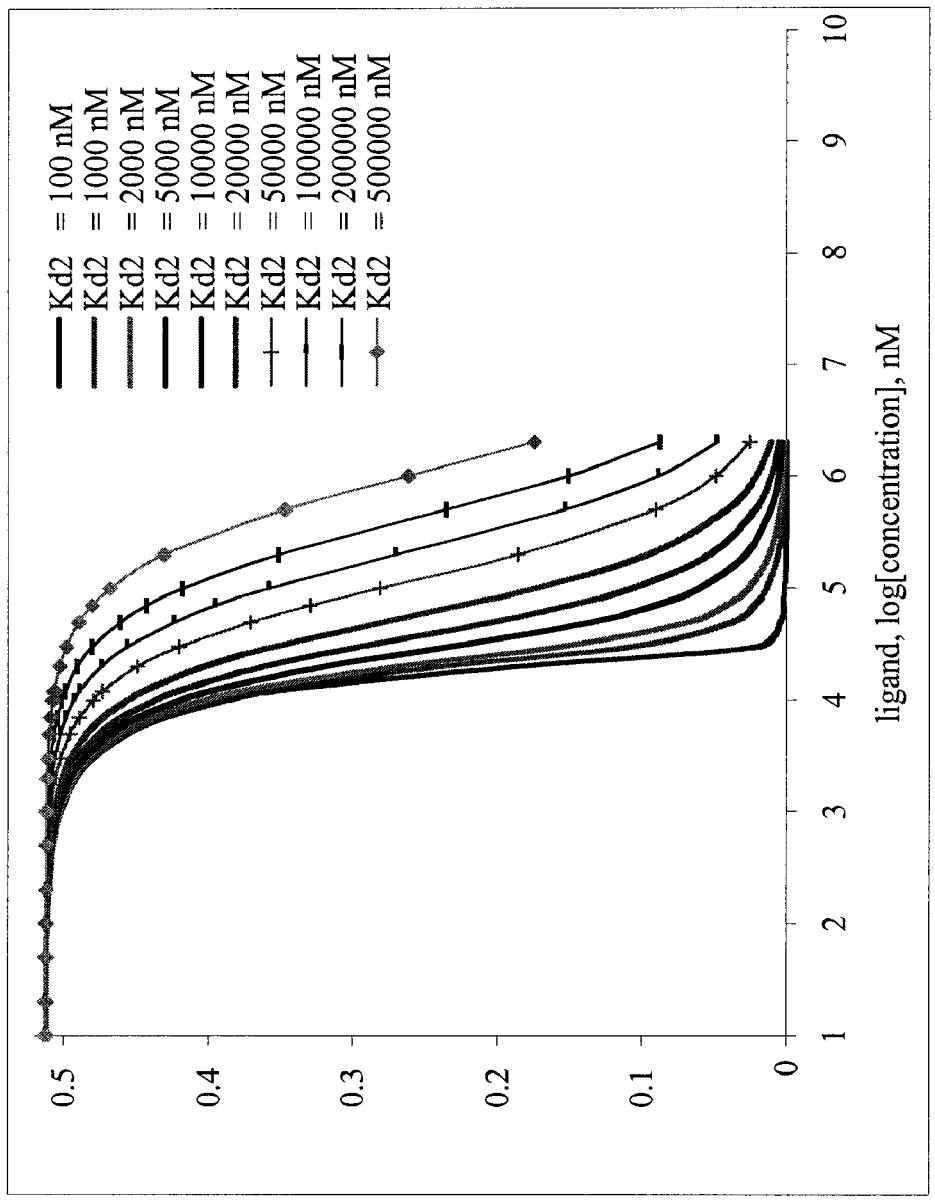
FIG. 15 is a graph of the fraction of bound probe versus ligand concentration as a function of ligand binding affinity (see Example 3, infra).

It is noted that this competitive binding assay does not allow accurate estimates of $K_d$ values much lower than the binding values of the fluorescent probe. FIG. 15 shows a graph of the fraction of bound probe versus ligand concentration as a function of ligand binding affinity. The narrowing of the space between curves below $K_d$ of 5 μM illustrates the limits of this assay.

Example 4

Cell-Cell Fusion Inhibition Assay

Cell-cell fusion (i.e., syncytium formation) was assayed by coculturing CHO[HIVe] (clone 7d2) cells expressing HXB2 envelope and tat with U373-MAGI cells (M. Emerman and A. Geballe, National Institutes of Health AIDS Research and Reference Reagent Program) in the presence of different concentrations of peptides 1-10. Cell fusion allows the expression of nuclear β-galactosidase from the U373-MAGI indicator cell line and can be quantitated by monitoring β-galactosidase activity. After an overnight incubation at 37° C. after coculture, β-galactosidase enzymatic activity was measured with the Mammalian β-galactosidase Chemiluminescent Assay Kit (Gal-Screen from Applied Biosystems). The peptide inhibitor concentrations at which activities were reduced by 50% ($IC_{50}$) relative to control samples lacking peptide inhibitor were calculated by fitting data to the variable-slope-sigmoid equation using the Prism program.

Example 5

Cytotoxity of Peptides on U373-MAGI

The cytotoxic effect of peptides 1-10 on U373-MAGI cells was measured in the presence of a series of diluted inhibitors for 6 days, and cell viability was quantitated with an MTT assay (Mosmann, "Rapid Colorimetric Assay for Cellular Growth and Survival: Application to Proliferation and Cytotoxicity Assays," *J. Immunol. Meth.* 65:55-63 (1983), which is hereby incorporated by reference in its entirety). No cytotoxicity was observed for peptides up to 200 μM concentrations.

Example 6

Peptide Design

The present gp41-targeting studies were begun by mimicking the 14-residue C-peptide (1) derived from gp41 that contains residues W628, W631, and I635, as shown in Table 3. This sequence would be expected to bind the gp41 hydrophobic pocket based on its crystal structure (shown in FIG. 1B) (Chan et al., "Core Structure of gp41 from the HIV Envelope Glycoprotein," *Cell* 89:263-73 (1997), which is hereby incorporated by reference in its entirety), but has been previously shown to be ineffective in cell-cell fusion assays (Sia et al., "Short Constrained Peptides That Inhibit HIV-1 Entry," *Proc. Nat'l Acad. Sci. U.S.A.* 99:14664-9 (2002), which is hereby incorporated by reference in its entirety).

TABLE 3

Binding affinities and cell fusion inhibition properties of peptides and HBS α-helices.

| Compound | Sequence[a] | | $K_d$ (μM)[b] | $EC_{50}$ (μM)[c] |
|---|---|---|---|---|
| C-peptide | NNMTWMEWDREINNYTSLI | (SEQ ID NO: 1) | — | — |
| 1 | AcMTWMEWDREINNYT | (SEQ ID NO: 14) | 37.4 ± 14.8[d] | — |
| 2 | XMTWMEWDREINNYT | (SEQ ID NO: 2) | 46.6 ± 14.6[d] | >>200 |
| 3 | XWAAWDKKI | (SEQ ID NO: 3) | >500 | >>200 |
| 4 | XAAAWEEWDKKI | (SEQ ID NO: 4) | >500 | >>200 |
| 5 | XWAAWDREINNYT | (SEQ ID NO: 5) | >500 | >>200 |
| 6 | XMTWEEWDKKIEEYT | (SEQ ID NO: 6) | 7.50 ± 1.70 | >>200 |
| 7 | XEMAWEEWDKKIEEYT | (SEQ ID NO: 7) | 146 ± 47.3 | >>200 |
| 8 | XNEMTWEEWDKKIEEYT | (SEQ ID NO: 8) | <5.00[e] | >>200 |
| 9 | XMTWEEWDKKIEEYTKKI | (SEQ ID NO: 9) | <5.00[e] | 42.7 ± 7.50 |
| 10 | AcMTWEEWDKKIEEYTKKI | (SEQ ID NO: 15) | <5.00[e] | >>200 |

[a]X denotes pentenoic acid residue. Residues that occupy a or d positions in the heptad are shown in bold.
[b]Binding affinity for IZN17 as calculated from a fluorescence polarization assay (Example 3) (Eckert & Kim, "Design of Potent Inhibitors of HIV-1 Entry from the gp41 N-Peptide Region," Proc. Nat'l Acad. Sci. U.S.A. 98: 11187-92 (2001), which is hereby incorporated by reference in its entirety).
[c]Inhibitory activity of peptides in a gp41-mediated cell-cell fusion assay monitoring syncytia formation (Eckert et al., "Inhibiting HIV-1 Entry: Discovery of D-Peptide Inhibitors That Target the gp41 Coiled-coil Pocket," Cell 99: 103-15 (1999), which is hereby incorporated by reference in its entirety).
[d]Precise measurements of the $K_d$ value not possible because the peptide aggregates at high concentrations.
[e]The competitive binding assay (Example 3) does not allow accurate estimates of $K_d$ values much lower than the binding values of the fluorescent probe.

A previously described fluorescence polarization assay was utilized to determine the in vitro binding affinity of unconstrained peptides and HBS helices for a stable model of the gp41 N-terminal three strand coiled-coil, IZN17, which contains the binding site for residues W628, W631, and I635 (see Example 3, supra) (Eckert & Kim, "Design of Potent Inhibitors of HIV-1 Entry from the gp41 N-Peptide Region," *Proc. Nat'l Acad. Sci. U.S.A.* 98:11187-92 (2001), which is hereby incorporated by reference in its entirety). A fluorescein-labeled C-peptide derivative (i.e., suc-MTWMEW-DREINNYTC$^{Flu}$ (SEQ ID NO: 10); peptide 12) containing residues 628-641 of gp41 was used as a probe. The competitive displacement of this probe by HBS helices afforded the $K_d$ value for each peptide shown in Table 3 and FIG. 16B (Stephens et al., "Inhibiting HIV Fusion with a β-Peptide Foldamer," *J. Am. Chem. Soc.* 127:13126-7 (2005), which is hereby incorporated by reference in its entirety). Peptide 12 bound IZN17 with a $K_d$ value of 24 µM, within range of the previously reported values (Sia et al., "Short Constrained Peptides That Inhibit HIV-1 Entry," *Proc. Nat'l Acad. Sci. U.S.A.* 99:14664-9 (2002); Stephens et al., "Inhibiting HIV Fusion with a β-Peptide Foldamer," *J. Am. Chem. Soc.* 127: 13126-7 (2005), which are hereby incorporated by reference in their entirety). The competition assay provided a binding affinity of 37 µM for peptide 1, which is also in range of reported values, although aggregation of the peptide made it difficult to obtain accurate $K_d$ values.

Circular dichroism spectroscopy (see Example 2, supra) suggested that 1 is unstructured or very weakly helical in 10% trifluoroethanol ("TFE") in PBS buffer (Sia et al., "Short Constrained Peptides That Inhibit HIV-1 Entry," *Proc. Nat'l Acad. Sci. U.S.A.* 99:14664-9 (2002), which is hereby incorporated by reference in its entirety). It was conjectured that stabilization of this peptide in helical conformation with the HBS approach may increase its helicity and affinity for IZN17. HBS α-helix 2 is roughly four times more helical than 1, as shown in FIG. 16A, but did not bind the target protein with higher affinity, as shown in Table 3. This suggests that there may be a complex interplay between helicity of the peptide and its binding affinity for the target (Martin, "Preorganization in Biological Systems: Are Conformational Constraints Worth the Energy?," *Pure Appl. Chem.* 79:193-200 (2007); Benfield et al., "Ligand Preorganization May Be Accompanied by Entropic Penalties in Protein-ligand Interactions," *Angew. Chem. Int'l Ed. Engl.* 45:6830-5 (2006), originally published at *Angew. Chem.* 118:6984-9 (2006), which are hereby incorporated by reference in their entirety). Results with the short peptide and constrained helix mirror those observed by Kim and coworkers (Sia et al., "Short Constrained Peptides That Inhibit HIV-1 Entry," *Proc. Nat'l Acad. Sci. U.S.A.* 99:14664-9 (2002), which is hereby incorporated by reference in its entirety), and prompted the design of a small library of HBS α-helices to identify sequences that bind IZN17 with higher affinity. A representative selection (i.e., peptides 2-9) of these HBS helices is shown in Table 3.

The limited solubility of short C-peptides in aqueous solutions has been proposed as a key reason for their inactivity (Otaka et al., "Remodeling of gp41-C34 Peptide Leads to Highly Effective Inhibitors of the Fusion of HIV-1 with Target Cells," *Angew. Chem. Int'l Ed. Engl.* 41:2937-40 (2002), originally published at *Angew. Chem.* 114:3061-4 (2002), which is hereby incorporated by reference in its entirety). To improve the solubility and helicity of constrained C-peptides, charged residues were incorporated at positions not expected to be involved in binding to IZN17 (Otaka et al., "Remodeling of gp41-C34 Peptide Leads to Highly Effective Inhibitors of the Fusion of HIV-1 with Target Cells," *Angew. Chem. Int'l Ed. Engl.* 41:2937-40 (2002), originally published at *Angew. Chem.* 114:3061-4 (2002), which is hereby incorporated by reference in its entirety). HBS α-helix 3 is the shortest peptide designed to contain the Trp/Trp/Ille motif necessary for binding. Two lysine residues were added within this sequence to improve solubility of the peptide. HBS α-helix 4 was designed such that the Trp/Trp/Ile motif would lie outside of the constraint in order to probe potential steric effects of the HBS constraints. A pair of glutamic acid and lysine residues were placed at i and i+4 positions to further stabilize the α-helical conformation through potential salt-bridging interactions (Marqusee & Baldwin, "Helix Stabilization by $Glu^-$ . . . $Lys^+$ Salt Bridges in Short Peptides of de Novo Design," *Proc. Nat.'l Acad. Sci. U.S.A.* 84:8898-902 (1987); Shi et al., "Stabilization of α-Helix Structure by Polar Side-chain Interactions: Complex Salt Bridges, Cation-pi Interactions, and C-H Em Leader O H-bonds," *Biopolymers* 60:366-80 (2001), which are hereby incorporated by reference in their entirety). Neither of these two HBS helices bound IZN17, suggesting that more contact points are needed to target the coiled-coil complex. HBS α-helix 5 contains tyrosine-638 in addition to the Trp/Trp/Ile residues. Tyr-638 occupies the d position in the heptad and is expected to directly contact the N-terminal three strand coiled-coil, as shown in FIG. 1C. The sequence of HBS α-helix 5 is similar to that of the parent compounds 1 and 2 but is missing N-terminal methionine-626 and threonine-627 residues. This compound also showed negligible affinity for IZN17, which was surprising because it was expected that 5 would bind IZN17 with similar affinity to that observed for 2. CD spectroscopy suggests that 2 and 5 are equally helical, as shown in FIG. 16A. The low binding affinity of 5 relative to 2 highlights the potential role of threonine-627, which occupies the g position in the heptad, as shown in FIG. 1C, and was not projected to contribute significantly to binding. Reintroduction of the Met-626 and Thr-627 residues and incorporation of charged residues at positions not expected to be involved in binding provided HBS α-helix 6, which bound IZN17 with a higher affinity than the parent HBS α-helix 2. The role of Thr-627 in the binding of HBS helices is also highlighted by HBS α-helix 7, in which this residue is replaced with an alanine residue. HBS α-helix 7 bound IZN17 by twenty-fold lower affinity than did 6.

Glutamic acid residues were placed at the N-terminus of HBS α-helices 7 and 8 to potentially stabilize the helix macrodipole. However, incorporation of this residue did not affect the binding affinity of these peptides.

HBS α-helices 8 and 9 were prepared to explore the effect of additional contact points (residues that occupy a or d positions in the heptad) on the amino and carboxy ends. Both HBS α-helices 8 and 9 consist of five residues that occupy a or d positions in the heptad and bind IZN17 with $K_d$ values <5 μM. Values for 8 and 9 represent upper limits in the present 1ZN17 assay, because competitive binding analysis does not allow accurate estimates of $K_d$ values much lower than the binding affinity of the fluorescent probe (see Example 3, supra) (Roehrl et al., "A General Framework for Development and Data Analysis of Competitive High-throughput Screens for Small-molecule Inhibitors of Protein-protein Interactions by Fluorescence Polarization," *Biochemistry* 43:16056-66 (2004), which is hereby incorporated by reference in its entirety). Although the 1ZN17 assay did not provide accurate values for the best HBS helices, it allowed for the qualitative evaluation of various constructs described herein. It was determined that a combination of the 1ZN17 binding assay and a gp41-mediated cell-cell fusion assay would provide a better gauge of the effectiveness of BBS helices as inhibitors of HIV fusion (Eckert et al., "Inhibiting HIV-1 Entry: Discovery of D-Peptide Inhibitors That Target the gp41 Coiled-coil Pocket," *Cell* 99:103-15 (1999), which is hereby incorporated by reference in its entirety).

Cell-cell fusion (i.e., syncytium formation) was assayed by co-culturing CHO[HIVe] (clone 7d2) cells expressing HXB2 envelope and tat (Kozarsky et al., "Glycosylation and Processing of the Human Immunodeficiency Virus Type 1 Envelope Protein," *J. Acquir. Immune Defic. Syndr.* 2:163-9 (1989), which is hereby incorporated by reference in its entirety) with U373-MAGI cells in the presence of different concentrations of the peptide inhibitors. Cell fusion allows the expression of nuclear β-galactosidase from the U373-MAGI indicator cell line and can be quantitated by monitoring β-galactosidase activity.

Inhibition of gp41-mediated cell fusion by short peptides is a challenging feat and has only been accomplished with a handful of synthetic peptides (Sia et al., "Short Constrained Peptides That Inhibit HIV-1 Entry," *Proc. Nat'l Acad. Sci. U.S.A.* 99:14664-9 (2002); Stephens et al., "Inhibiting HIV Fusion with a β-Peptide Foldamer," *J. Am. Chem. Soc.* 127: 13126-7 (2005); Eckert et al., "Inhibiting HIV-1 Entry: Discovery of D-Peptide Inhibitors That Target the gp41 Coiled-coil Pocket," *Cell* 99:103-15 (1999), which are hereby incorporated by reference in their entirety). It was found that only HBS α-helix 9 inhibited cell fusion with an $EC_{50}$ value of 43 μM, as shown in FIG. 16C. This value is comparable to those measured for side chain constrained α-helices (Sia et al., "Short Constrained Peptides That Inhibit HIV-1 Entry," *Proc. Nat'l Acad. Sci. U.S.A.* 99:14664-9 (2002), which is hereby incorporated by reference in its entirety), cyclic D-peptides (Eckert et al., "Inhibiting HIV-1 Entry: Discovery of D-Peptide Inhibitors That Target the gp41 Coiled-coil Pocket," *Cell* 99:103-15 (1999), which is hereby incorporated by reference in its entirety), aromatic foldamers (Ernst et al., "Design of a Protein Surface Antagonist Based on α-Helix Mimicry: Inhibition of gp41 Assembly and Viral Fusion," *Angew. Chem. Intl Ed. Engl.* 41:278-81 (2002), originally published at *Angew. Chem.* 114:282-91 (2002), which is hereby incorporated by reference in its entirety), and β-peptide foldamers (Stephens et al., "Inhibiting HIV Fusion with a β-Peptide Foldamer," *J. Am. Chem. Soc.* 127:13126-7 (2005), which is hereby incorporated by reference in its entirety). Other HBS α-helices (2-8) did not provide any hints of cell fusion inhibition at concentrations up to 200 μM. Unconstrained peptide 10, which bound IZN17 with a similar affinity as 9, remained ineffective in the cell culture assay. This result potentially reflects the proteolytic instability of the unconstrained peptide, as stabilization of peptides in α-helical conformation is expected to enhance their resistance to proteases (Tyndall et al., "Proteases Universally Recognize β Strands in Their Active Sites," *Chem. Rev.* 105:973-99 (2005), which is hereby incorporated by reference in its entirety). Improvements in the proteolytic stability of HBS α-helices as compared to their unconstrained counterparts has previously been reported (Wang et al., "Enhanced Metabolic Stability and Protein-binding Properties of Artificial α Helices Derived from a Hydrogen-bond Surrogate: Application to Bcl-xL," *Angew. Chem. Intl Ed. Engl.* 44:6525-9 (2005), originally published at *Angew. Chem.* 117:6683-7 (2005), which is hereby incorporated by reference in its entirety).

In summary, through rational design and synthesis, an artificial α-helix (9) that inhibits gp41-mediated cell fusion has been developed. As formation of coiled-coil assemblies is a prerequisite for the fusion of several classes of viruses to their host cells (Dimitrov, "Virus Entry: Molecular Mechanisms and Biomedical Applications," *Nat. Rev. Microbiol.* 2:109-22 (2004) which is hereby incorporated by reference in its entirety), this work suggests that HBS helices may be effective scaffolds for the generation of small molecule inhibitors or antigens against these viruses (English et al., "Rational Development of (3-Peptide Inhibitors of Human Cytomegalovirus Entry," *J. Biol. Chem.* 281:2661-7 (2006); Shepherd et al., "Modular α-Helical Mimetics with Antiviral Activity Against Respiratory Syncitial Virus," *J. Am. Chem. Soc.* 128: 13284-9 (2006), which are hereby incorporated by reference in their entirety).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A peptide having a stable, internally-constrained alpha-helix, wherein said alpha helix is constrained by a crosslink formed by a carbon-carbon bond-forming reaction, and further wherein the peptide mimics at least a portion of a gp41 C-peptide helix derived from human immunodeficiency virus, wherein the peptide is an inhibitor of viral infectivity, and wherein the peptide comprises the amino acid sequence of SEQ ID NO: 9, and has an internally-constrained alpha-helix spanning residues 1 through 4 of SEQ ID NO: 9.

2. The peptide of claim 1, wherein the carbon-carbon bond-forming reaction is metathesis.

3. The peptide according to claim 1, wherein the peptide mimics the WWI region of the gp41 C-peptide helix.

4. The peptide according to claim 1, wherein the peptide comprises the formula:

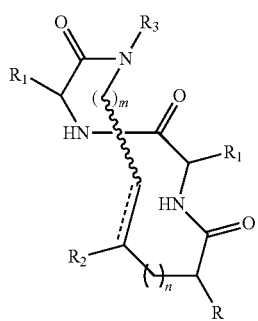

wherein
----- is a single or double carbon-carbon bond;
~~~~ is a single bond and is cis or trans when ----- is a double bond;
n is 1 or 2;
m is zero or any positive integer;
R is hydrogen, an amino acid side chain, an alkyl group, or an aryl group;
$R_1$ is an amino acid side chain, an alkyl group, or an aryl group;
$R_2$ is an amino acid, second peptide, —OR, —$CH_2NH_2$, an alkyl group, an aryl group, hydrogen, or a group having a formula

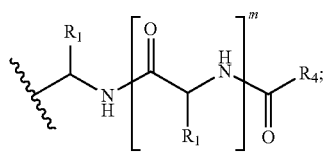

where $R_4$ is an amino acid, third peptide, —OR, —$NH_2$, an alkyl group, or an aryl group; and $R_3$ is a fourth peptide.

5. A pharmaceutical composition comprising a peptide according to claim 1 and a pharmaceutically acceptable vehicle.

* * * * *

SEQUENCE LISTING

```
<160> NUMBER OF SEQ ID NOS: 17

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Asn Met Thr Trp Met Glu Trp Asp Arg Glu Ile Asn Asn Tyr Thr
1               5                   10                  15

Ser Leu Ile

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid
```

```
<400> SEQUENCE: 2

Xaa Met Thr Trp Met Glu Trp Asp Arg Glu Ile Asn Asn Tyr Thr
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid

<400> SEQUENCE: 3

Xaa Trp Ala Ala Trp Asp Lys Lys Ile
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid

<400> SEQUENCE: 4

Xaa Ala Ala Ala Trp Glu Glu Trp Asp Lys Lys Ile
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid

<400> SEQUENCE: 5

Xaa Trp Ala Ala Trp Asp Arg Glu Ile Asn Asn Tyr Thr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid

<400> SEQUENCE: 6

Xaa Met Thr Trp Glu Glu Trp Asp Lys Lys Ile Glu Glu Tyr Thr
1               5                   10                  15

<210> SEQ ID NO 7
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid

<400> SEQUENCE: 7

Xaa Glu Met Ala Trp Glu Glu Trp Asp Lys Lys Ile Glu Glu Tyr Thr
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid

<400> SEQUENCE: 8

Xaa Asn Glu Met Thr Trp Glu Glu Trp Asp Lys Lys Ile Glu Glu Tyr
1               5                   10                  15

Thr

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pentenoic acid

<400> SEQUENCE: 9

Xaa Met Thr Trp Glu Glu Trp Asp Lys Lys Ile Glu Glu Tyr Thr Lys
1               5                   10                  15

Lys Ile

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Thr Trp Met Glu Trp Asp Arg Glu Ile Asn Asn Tyr Thr Cys
1               5                   10                  15

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 11

His Thr Thr Trp Met Glu Trp Asp Arg Glu Ile Asn Asn Tyr Thr Ser
1               5                   10                  15

Leu Ile His Ser Leu Ile Glu Glu Ser Gln Asn Gln Gln Glu Lys Asn
            20                  25                  30

Glu Gln Glu Leu Leu Glu
        35

<210> SEQ ID NO 12
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Leu Leu Ser Gly Ile Val Gln Gln Gln Asn Asn Leu Leu Arg Ala
1               5                   10                  15

Ile Glu Ala Gln Gln His Leu Leu Gln Leu Thr Val Trp Gly Ile Lys
            20                  25                  30

Gln Leu Gln Ala Arg Ile Leu Ala
        35                  40

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid

<400> SEQUENCE: 13

Trp Xaa Xaa Trp Xaa Xaa Xaa Ile Xaa Xaa Tyr Xaa Xaa Xaa Ile
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Thr Trp Met Glu Trp Asp Arg Glu Ile Asn Asn Tyr Thr
1               5                   10

<210> SEQ ID NO 15
<211> LENGTH: 17
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 15

Met Thr Trp Glu Glu Trp Asp Lys Lys Ile Glu Glu Tyr Thr Lys Lys
1               5                   10                  15

Ile

<210> SEQ ID NO 16
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ile Lys Lys Glu Ile Glu Ala Ile Lys Lys Glu Gln Glu Ala Ile Lys
1               5                   10                  15

Lys Lys Ile Glu Ala Ile Glu Lys Leu Leu Gln Leu Thr Val Trp Gly
            20                  25                  30

Ile Lys Gln Leu Gln Ala Arg Ile Leu
        35                  40

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid or not present

<400> SEQUENCE: 17

Trp Xaa Xaa Trp Xaa Xaa Xaa Ile Xaa Xaa Tyr Xaa Xaa Xaa Ile Xaa
1               5                   10                  15
```